US010452035B2

United States Patent
Goemann-Thoss et al.

(10) Patent No.: US 10,452,035 B2
(45) Date of Patent: Oct. 22, 2019

(54) LABORATORY INSTRUMENT FOR INSTRUMENT-CONTROLLED TREATMENT OF AT LEAST ONE LABORATORY SAMPLE

(71) Applicant: Eppendorf AG, Hamburg (DE)

(72) Inventors: Wolfgang Goemann-Thoss, Hamburg (DE); Wolf Wente, Hamburg (DE); Andreas Thieme, Hamburg (DE); Jan-Gerd Frerichs, Norderstedt (DE); Christiane Markau, Hamburg (DE); Jan-Hendrik Hacker, Hamburg (DE)

( * ) Notice: Subject to any disclaimer, the term of this patent is extended or adjusted under 35 U.S.C. 154(b) by 961 days.

(21) Appl. No.: 14/508,722

(22) Filed: Oct. 7, 2014

(65) Prior Publication Data

US 2015/0105877 A1 Apr. 16, 2015

(30) Foreign Application Priority Data

Oct. 7, 2013 (EP) .................... 13 004 811

(51) Int. Cl.
*G05B 15/02* (2006.01)
*G01N 35/00* (2006.01)
*H04L 29/08* (2006.01)

(52) U.S. Cl.
CPC ....... *G05B 15/02* (2013.01); *G01N 35/00722* (2013.01); *H04L 67/10* (2013.01); *G01N 35/00871* (2013.01); *G01N 2035/00821* (2013.01); *G01N 2035/00881* (2013.01); *G01N 2035/00891* (2013.01)

(58) Field of Classification Search
CPC .................................... G05B 15/02
USPC ........................................ 700/83
See application file for complete search history.

(56) References Cited

U.S. PATENT DOCUMENTS

| 6,544,476 B1 * | 4/2003 | Mimura ........... G01N 35/00722 422/63 |
| 2002/0032762 A1 | 3/2002 | Price et al. |
| 2002/0135678 A1 | 9/2002 | Bacus et al. |

(Continued)

FOREIGN PATENT DOCUMENTS

| EP | 0952452 A1 | 10/1999 |
| EP | 0973115 A2 | 1/2000 |

(Continued)

OTHER PUBLICATIONS

U.S. Appl. No. 14/508,703 (U.S. Publication No. US 20150125961 A1), entitled, "Laboratory instrument with access control device and method for instrument-controlled treatment of laboratory samples, laboratory instrument and method," filed Oct. 7, 2014, of Goemann-Thoss, et al.

(Continued)

*Primary Examiner* — James D. Rutten
(74) *Attorney, Agent, or Firm* — Todd A. Lorenz

(57) ABSTRACT

The invention relates to a configuration control device for a laboratory instrument, a laboratory instrument with a configuration control device for instrument-controlled treatment of at least one laboratory sample and a method for configuring the laboratory instrument by means of the configuration control device. By using user-dependent configuration data, the requirement for the user of having to perform a completely manual configuration of the laboratory instrument, which is effected by the user-dependent configuration data, is dispensed with.

10 Claims, 7 Drawing Sheets

(56) References Cited

U.S. PATENT DOCUMENTS

| | | | |
|---|---|---|---|
| 2003/0141116 A1* | 7/2003 | Nuesch | G01G 23/00 177/25.11 |
| 2004/0171171 A1 | 9/2004 | Appoldt et al. | |
| 2005/0014285 A1 | 1/2005 | Miller | |
| 2005/0112542 A1 | 5/2005 | West | |
| 2005/0131734 A1 | 6/2005 | Sugiyama | |
| 2005/0159982 A1 | 7/2005 | Showalter et al. | |
| 2005/0192908 A1 | 9/2005 | Jorimann et al. | |
| 2006/0148063 A1* | 7/2006 | Fauzzi | G01N 1/31 435/286.4 |
| 2006/0173575 A1* | 8/2006 | Lefebvre | G01N 1/31 700/231 |
| 2006/0242276 A1 | 10/2006 | Price et al. | |
| 2007/0143465 A1 | 6/2007 | Gonzalez et al. | |
| 2007/0233303 A1* | 10/2007 | Naito | G01N 35/00584 700/108 |
| 2007/0255756 A1 | 11/2007 | Satomura et al. | |
| 2008/0059472 A1 | 3/2008 | Yamamoto et al. | |
| 2008/0256227 A1 | 10/2008 | Malin | |
| 2010/0106427 A1 | 4/2010 | Fukuma et al. | |
| 2010/0271479 A1 | 10/2010 | Heydlauf | |
| 2011/0246215 A1 | 10/2011 | Postma et al. | |
| 2013/0045473 A1 | 2/2013 | Duerr et al. | |
| 2013/0159135 A1 | 6/2013 | Jones et al. | |

FOREIGN PATENT DOCUMENTS

| | | | | |
|---|---|---|---|---|
| EP | 1248170 | A1 | 10/2002 | |
| EP | 1840576 | A2 | 10/2007 | |
| EP | 1981245 | A1 | 10/2008 | |
| EP | 2182364 | A2 | 5/2010 | |
| EP | 2182365 | A2 | 5/2010 | |
| EP | 2299277 | A1 | 3/2011 | |
| EP | 2450711 | A1 | 5/2012 | |
| WO | WO 9411838 | A1 * | 5/1994 | ....... G01N 35/00732 |
| WO | WO 2008012104 | A2 | 1/2008 | |
| WO | WO 2009085534 | A1 | 7/2009 | |
| WO | WO 2012/045415 | A1 | 4/2012 | |

OTHER PUBLICATIONS

U.S. Appl. No. 14/508,716 (U.S. Publication No. US 20150104796 A1), entitled, "System comprising at least two laboratory instruments for instrument-controlled handling of a partial problem in a treatment process containing treatments of at least one laboratory sample, laboratory instrument and method," filed Oct. 7, 2014, of Goemann-Thoss, et al.

U.S. Appl. No. 14/508,724 (U.S. Publication No. US 20150127270 A1), entitled, "Laboratory instrument, system and method for instrument-controlled treatment of at least one laboratory sample using at least one consumable," filed Oct. 7, 2014, of Goemann-Thoss, et al.

* cited by examiner

LABORATORY INSTRUMENT FOR INSTRUMENT-CONTROLLED TREATMENT OF AT LEAST ONE LABORATORY SAMPLE

The invention relates to a configuration control device for a laboratory instrument, a laboratory instrument with the configuration control device for instrument-controlled treatment of at least one laboratory sample and a method for configuring the laboratory instrument by means of the configuration control device.

Laboratory instruments are used in chemical, biological, biochemical, medical or forensic laboratories to handle laboratory samples, in particular liquid laboratory samples, with great efficiency. Such laboratory instruments at least partly automate treatment steps which would otherwise have to be performed manually and thus increase the speed, precision and reliability of these treatments. A treatment of laboratory samples, which are usually in liquid form, may be directed to modifying or examining or analysing these laboratory samples, in particular the composition thereof, in a physical, chemical, biochemical or other manner.

Generally, a multiplicity of hardware and/or software settings are undertaken by the user when operating the aforementioned laboratory instruments before the desired treatment of a sample can be performed. Firstly, this relates to settings, by means of which the general mode of operation of the instrument is influenced, and, secondly, this relates to settings, which are intended to have a direct effect on the desired treatment or define the latter. The laboratory instruments usually comprise a treatment apparatus for instrument-controlled treatment of the at least one laboratory sample. They often have a program control, by means of which a user of the laboratory instrument can set the treatment to be performed by setting the desired program parameters. The program parameters are set by means of an operating unit of the laboratory instrument, which enables the input and output of information, in particular of values of the program parameters. User errors when entering parameters is a factor which continuously reduces the result quality and productivity of a laboratory.

It is an object of the present invention to make available a configuration control device for a laboratory instrument, the laboratory instrument with a configuration control device, and a method for configuring the laboratory instrument by means of the configuration control device, by means of which the productivity in a laboratory can be improved.

The invention achieves this object by means of, in particular, the configuration control device in accordance with claim 1, the laboratory instrument in accordance with claim 7 and the method according to claim 14. Preferred embodiments of the invention are, in particular, the subject matter of the dependent claims.

By using user-dependent configuration data, the requirement of having to perform a completely manual configuration of the laboratory instrument, which is effected by the user-dependent configuration data, is dispensed with. On the other hand, the provision of the configuration control device can bring about a user-dependent design of the elements of a user interface apparatus, in particular of operating elements of the laboratory instrument, in particular of the user interface of an indication apparatus. By means of such measures, it is possible to reduce input errors and increase the productivity in a laboratory.

A configuration of an instrument is understood to mean the setting of at least one modifiable parameter which has an effect on the functionality of the instrument. This effect can be restricted in time or can be permanent, and can depend on other conditions, in particular parameters. Preferably, setting the at least one parameter is a repeatable process, in particular an unrestrictedly repeatable process. However, the process can also denote a single instance of setting a parameter.

A configuration control device is understood to mean an instrument or an instrument component, the function or functions of which have an effect on the configuration of the instrument or of another instrument, in particular of the laboratory instrument. The configuration control device is or can be connected to this other instrument via interface apparatuses. The configuration control device can be a separate instrument or an instrument that is separable from the other instrument, in particular from the laboratory instrument, i.e. it is a module. However, it is particularly preferred for the configuration control device to be integrated into the other instrument, in particular into the laboratory instrument, in particular into the control apparatus of the other instrument, in particular of the laboratory instrument. In particular, the control apparatus of the configuration control device can be integrated into the other instrument, in particular into the laboratory instrument, in particular into the control apparatus of the other instrument, in particular of the laboratory instrument. One, some or all functions of the configuration control device can be realized as software functions. One, some or all functions of the configuration control device can, in particular, be realized as executable program code, which can be executed by a control apparatus.

Configuration data are data by means of which the configuration of a configurable instrument, in particular of the laboratory instrument, can be influenced, in particular set.

In particular, configuration data can be instrument data. Instrument data are understood to mean data, by means of which the functionality of an instrument, in particular of the laboratory instrument according to the invention, can be influenced, in particular set. Instrument data are preferably suitable for influencing the control of the display of an optionally provided user interface of the laboratory instrument according to the invention.

A laboratory instrument, in particular the control apparatus thereof, is preferably configured to configure the course of the treatment before the treatment is started. In particular, this can be brought about by means of a process program. In order to perform the treatment, at least one parameter generally needs to be determined, in particular by the user. However, it is also possible for the laboratory instrument and/or the configuration control device to be configured to determine this at least one parameter, in particular to set it in a user-dependent manner. The at least one parameter can be a program parameter, in particular a user parameter.

The term "treatment" means, in particular, that a laboratory sample, which is usually in liquid form, is moved and/or transported and/or examined and/or modified, in particular modified physically, chemically, biochemically or in another way in terms of the composition thereof.

The configuration process for an individual treatment is dependent on the type of treatment. Preferably, the configuration procedure for an individual treatment is user-dependent. The laboratory instrument, in particular the control apparatus thereof, is preferably configured to perform the configuration process for an individual treatment in a user-dependent manner on the basis of the configuration data. It is possible for a user-dependent configuration process to occur in the case of an individual treatment for the same type of treatment. Here, a user-dependent selection of user parameters can be offered to the user for setting purposes and/or a user-dependent user interface can be displayed. The configuration data, in particular the instrument data, can, inter alia, determine the course of the configuration of a treatment by virtue of, in particular, influencing a process program which is characteristic for the selected type of treatment. The instrument data preferably influence the design of the user interface, which is indicated on an indication apparatus, in particular a display, during the operation of the laboratory instrument, in particular during the definition of a treatment, in particular of a process program. This display apparatus is, in particular, a component of the configuration control device or a user interface apparatus, which can be a component of the configuration control device, of the laboratory instrument or of an external data processing apparatus.

Data, by means of which the performance of a treatment is directly influenced or defined, are preferably not instrument data. Instrument data are preferably not process data and/or not program parameters and/or not user parameters.

However, configuration data can also be data, or comprise such data, by means of which the individual, planned treatment of the at least one laboratory sample, in particular the control of the at least one treatment apparatus of the laboratory instrument, can be influenced, in particular set, in the laboratory instrument according to the invention. Such data are also referred to as process data in the present case. This influencing, in particular setting, preferably occurs at least for a planned treatment. However, it can also occur during a treatment. Preferably, the configuration data are set prior to the start of a treatment. It can also occur during the treatment or thereafter. Configuration data can be program parameters or can determine program parameters.

Predetermined, user-dependent configuration data are preferably stored in a storage apparatus. The latter can be a component of the configuration control device, of the laboratory instrument and/or of an external data processing apparatus, in particular of a computer, in particular of a server. It is preferable for the laboratory instrument, in particular the control apparatus thereof, to be configured, while the laboratory instrument is being operated by a user, in particular while the manual configuration is set by a user, to acquire configuration data and store the latter as user-dependent configuration data, in particular in the storage apparatus. Then, the user can transmit these configuration data from the storage apparatus to another laboratory instrument if he wishes to use these configuration data on a different laboratory instrument. What he is spared in the process is needing once again to set all configuration data manually.

It is also possible for a user to be assigned user-dependent configuration data as a function of his role, which was assigned to him when logging into the laboratory instrument.

User-dependent procedure means that a method is followed either dependent on a user, in particular a class, group or role of the user, which can be distinguished by various aspects, or in a user-individual manner. A user-dependent display on the user interface means, in particular, that use is made of a specific user interface, in particular a request mask, which is assigned to said user.

The user class or role can be established by means of a database. For an individual, the user class can emerge from his specialist qualification, his professional standing in the company or else by the assignment according to a different criterion. The criterion can also be bound to a measurement which is performed by at least one sensor that is signal connected to the control apparatus and can be a component of the laboratory machine. This measurement can, in particular, determine a personalized measurement parameter, in particular establish a body parameter of the person. As a result of this information it is possible, in particular, to adapt the laboratory instrument to the body dimension, e.g. to the body height of the person, in order, for example, to adapt the setting of the laboratory instrument automatically to this body dimension. This can result in improved ergonomics. The sensor can also comprise a microphone, by means of which the speech of the user is acquired, in particular recorded. The speech data can be used and/or evaluated for generating a log file. Preferably, the configuration control device, in particular the control apparatus thereof, comprises a speech recognition apparatus. The speech acquired by the sensor can be analysed and evaluated by means of the speech recognition apparatus, with speech data being established. The speech data can be used to acquire a control command, by means of which the control of the laboratory instrument and/or of the configuration control device can be influenced. In particular, the speech data can be evaluated in order to establish the speech of the user. The user interface can be adapted as a function of the speech, by virtue of the text displayed on the user interface and/or the speech output by means of a loudspeaker of the laboratory instrument being adapted to the speech established by the speech analysis.

The invention relates, in particular, to a user-dependent user interface, in particular a user-dependent request mask, and to a method for user guidance, in particular for the user-dependent requesting of user parameters by means of this user-dependent user interface.

A user interface is a graphical user interface, which is or can be preferably displayed on the screen of the user interface apparatus. In particular, the screen can be a touch-sensitive screen ("touchscreen"). The user interface can be an indication page, by means of which information is indicated and/or read.

A request mask is an indication page for display on a screen of the user interface apparatus, with at least one indication region for indicating the variable value of a program parameter or user parameter. Such an indication page has static regions ??? which do not change while being displayed within the indication page. Such an indication page of the request mask furthermore comprises at least one indication region, the display of which while being displayed within the indication page can change, e.g. by virtue of the value changing automatically, e.g. when indicating a time in this indication region, or by changing as a function of a user entry, e.g. the indication of a value of a user parameter or another program parameter. A user parameter is a program parameter selected by the user. A parameter which is used by the control apparatus for controlling a treatment is a program parameter. A user parameter is also referred to as first program parameter, or as program parameter of the first type. Program parameters which are not entered by the user are referred to as second program parameters. Second program parameters are set by the control apparatus by calculation or by values which are predetermined and stored in a data storage medium. Preferably, the configuration control device is embodied to control the configuration of the laboratory instrument in such a way that the user-dependent configuration data set which first program parameters and which second program parameters are used when setting a treatment, in particular when defining a process program. As a result, it is possible, in particular, to leave an inexperienced user with a smaller number of first program parameters to be selected than an experienced user and, secondly, it is possible, in particular, to prescribe a greater number of second program parameters for an inexperienced user than for an experienced user. As a result, the inexperienced user will make fewer mistakes when operating the laboratory instrument and the experienced user is allowed greater flexibility when operating the laboratory instrument. Both measures will increase the productivity in a laboratory and lower the costs.

The indication page itself can be movable, by virtue of, e.g., being able to be scrolled on the screen, particularly in the context of only a partial display.

A data connection connects, in particular, two data-processing units, in particular two data processing apparatuses, in such a way that data can be interchanged, either unidirectional or bidirectionally, between the units. The data connection can be realized with, or without, cables, in particular as a wireless connection. A remote data connection connects, in particular, two data processing units, in particular two data processing apparatuses, which are arranged at a distance from one another, which are therefore, in particular, not components of the same instrument, in particular of the same configuration control device, access control device, user Interface apparatus or of the same laboratory instrument if the aforementioned instruments are embodied as separate instruments. A data connection, in particular a remote data connection, from one instrument to another instrument is preferably realized by a direct connection between the two instruments or by means of an indirect connection between the two instruments such that a third instrument is switched between the two instruments in order to forward the data. In particular, a remote data connection can be realized via a network of computers, in the case of which the instruments connected via the remote data connection are connected via the network. The network can be a restricted network, e.g. an intranet, or a world-wide network, in particular the Internet.

Preferably, in a first preferred configuration of the configuration control device according to the invention, the at least one interface apparatus of the configuration control device is embodied to establish at least one third data connection with at least one external data processing apparatus, in particular a server, which, in particular, comprises a storage apparatus on which configuration data can be stored, Preferably, the control apparatus of the configuration control device is embodied to receive configuration data via the at least one third data connection.

Preferably, in a second preferred configuration of the configuration control device according to the invention which, in particular, may comprise the first configuration, the control apparatus of the configuration control device is embodied to evaluate the configuration data received via the at least one third data connection and to assign user-dependent configuration data to the identified user, which configuration data can be used for the user-dependent treatment of the at least one laboratory sample.

Preferably, in a third preferred configuration of the configuration control device according to the invention which, in particular, may comprise the first or second configuration, the control apparatus of the configuration control device is embodied to transmit identification data, which identify the user, to the at least one external data processing apparatus via the at least one third data connection and to receive the configuration data assigned to the identified user as these user-dependent configuration data for the laboratory instrument from the external data processing apparatus.

Preferably, in a fourth preferred configuration of the configuration control device according to the invention which, in particular, may comprise the first, second or third configuration, the configuration control device comprises a user interface apparatus in order to enable the identified user access to the laboratory instrument. Preferably, the access control device is configured to enable the identified user access by means of the user interface apparatus to the laboratory machine via the first data connection.

Preferably, in a fifth preferred configuration of the configuration control device according to the invention which, in particular, may comprise the first, second, third or fourth configuration, the access control device is configured only then to enable the identified user access to the laboratory instrument, in particular to at least one function of the laboratory instrument. In accordance with a sixth preferred configuration of the configuration control device according to the invention which, in particular, may comprise the first, second, third, fourth or fifth configuration, the access control device is configured to enable the identified the user access to the laboratory instrument only if at least one predetermined access condition in relation to the identified user is satisfied. This access condition can use the result of checking the role of the user, the qualification of the user, a booking entry in a booking database, a time and/or a request for release via a data connection, which is performed by the laboratory instrument.

The invention furthermore relates to a laboratory instrument for instrument-controlled treatment of at least one laboratory sample, comprising:
 a configuration control device according to one of the preceding claims; and
 at least one treatment apparatus for instrument-controlled treatment of the at least one laboratory sample;
 a control apparatus for the user-dependent control of the laboratory instrument, in particular of the treatment apparatus;
wherein the control apparatus of the laboratory instrument is configured to receive user-dependent configuration data from the configuration control device and to control the laboratory instrument in accordance with the user-dependent configuration data.

Preferably, in a first preferred configuration of the laboratory instrument according to the invention, the control apparatus of the laboratory instrument is configured to use user-dependent configuration data, in particular instrument data, as a function of the identified user. The configuration data preferably determine a set of user-dependent program parameters, by means of which a program-controlled treatment by means of the treatment apparatus can be controlled in a user-dependent manner.

Preferably, in a second preferred configuration of the laboratory instrument according to the invention which, in particular, may comprise the first configuration of the laboratory instrument, the laboratory instrument comprises a user interface apparatus for entering data by the user. Preferably, the user interface apparatus comprises at least one indication apparatus for indicating information for the user on at least one graphical user interface, wherein the control apparatus is embodied, in particular, to control the indication apparatus in such a way that a user-dependent design of the user interface is used, depending on the identified user and using the user-dependent configuration data.

Preferably, in a third preferred configuration of the laboratory instrument according to the invention which, in particular, may comprise the second configuration of the laboratory instrument, the control apparatus of the laboratory instrument is configured to control the treatment as a function of at least one user parameter selected by a user and, in particular, to acquire at least one user parameter in a user-dependent request process by means of the user interface apparatus, by virtue of i) presenting to the user at least one user-dependent, i.e., for example, dependent on the user class, e.g. qualification, or else dependent on an individual, request mask, i.e., in particular, an indication page with at least one indication region for indicating the variable value of a program parameter or user parameter, on the user interface and preferably ii) at least one user parameter being acquired by acquiring at least one entry of the user in the at least one request mask.

The invention furthermore relates to a system for instrument-controlled treatment of at least one laboratory sample, comprising at least one laboratory instrument according to the invention and at least one external data processing apparatus, in particular a server, which are interconnected for interchanging data, in particular configuration data.

Preferably, in a first preferred configuration of the system according to the invention, the system comprises at least a first and a second laboratory instrument according to the invention, which are respectively configured to process first user-dependent configuration data, which can be used for the user-dependent control of the first laboratory instrument, and which can also be used for the user-dependent control of the second laboratory instrument.

Preferably, in a second preferred configuration of the system according to the invention which, in particular, may comprise the first configuration of the system, the system comprises an external data processing apparatus and a user interface apparatus, which can be a component of the external data processing apparatus, wherein user-dependent configuration data can be generated from the entries of the user by means of the user interface apparatus.

Within the scope of the present invention, a control apparatus generally comprises, in particular, a data processing apparatus, in particular a computer unit (CPU) for processing data and/or a microprocessor, or said control apparatus is a data processing apparatus. A computer unit of the control apparatus of a laboratory instrument is preferably also configured for controlling the treatment process and/or the individual treatments.

The control apparatus of the laboratory instrument and/or the access control and/or the optional user interface apparatus—in particular all of these—can be integrated in a physical instrument unit but can also in each case be independent physical instrument units. A physical instrument unit can, in particular, be a module which is or can be connected to the laboratory instrument. The control apparatus of the laboratory instrument and/or the access control device and/or the optional user interface apparatus or components of these components can also be implemented by software functions or can, in particular, be available as program code. By way of example, a laboratory instrument can comprise a computer which, in combination with software functions, in each case at least partly implements the control apparatus of the laboratory instrument and/or the optional access control device and/or the optional user interface apparatus. By way of example, if the access control device is integrated into the laboratory instrument, the access control device itself may be part of the control apparatus of the laboratory instrument or be implemented by means of the control apparatus, in particular by software functions, in particular at least partly as executable program code.

A communication apparatus is preferably configured for the transmission and/or reception of data, in particular the data interchange via a data connection provided by the communication apparatus, in particular a remote data connection to a remote instrument. In particular, the instrument arranged at a distance from a laboratory instrument is also referred to as "remote instrument" or external instrument. In particular, a data processing apparatus which is not a component of a laboratory instrument is also referred to as an external data processing apparatus. The data connection, in particular the remote data connection, can be established over a restricted network of computers (in particular an intranet) or over a worldwide network of computers (in particular the Internet). The data connection, in particular the remote data connection, can also be established over a wireless connection. The data connection, in particular the remote data connection, can, in particular, be established over a mobile communications connection.

Every user can establish a first data connection with the access control device by means of the same user interface apparatus or a plurality of users can establish a first data connection with the access control device by means of different user interface apparatuses. A user interface apparatus can be a component of the access control device. An access control device can be a component of the user interface apparatus. A user interface apparatus can be a component of a laboratory instrument. A user interface apparatus preferably comprises in each case: a control apparatus for a user interface apparatus; a communication apparatus for establishing a data connection to a laboratory instrument by means of an interface apparatus of same; an input apparatus for acquiring user inputs of a user; an output apparatus, in particular an indication unit and/or a display, for outputting information to the user. Here, the control apparatus of the user interface apparatus is preferably configured to interchange data with the laboratory instrument via the data connection, which data were obtained from the user inputs and, in the laboratory instrument according to the invention, cause the second user to be granted authorizations and/or access permissions on the laboratory instrument according to the invention such that a simultaneous log on and/or the simultaneous access of a first and at least a second user on the laboratory instrument according to the invention with respectively assigned access permissions to functions of the laboratory instrument can be controlled via the interface apparatus.

In a laboratory instrument, the access control device enables the access of one or more further users to the laboratory device to be controlled when a first user is already logged on and the session of said first user is still running on the laboratory instrument, i.e. when the access of the further user is still active. As a result of this embodiment, the laboratory instrument can be used more efficiently and the productivity of the laboratory can be improved. The access control device can be integrated into the control apparatus of the laboratory instrument. The access control device can be embodied as a module. The access control device can be a component of the configuration control device. The configuration control device can be a component of the access control device. Access control device and configuration control device can be disposed in one module.

A module can, in particular, comprise the access control device and/or the configuration control device and/or a user interface apparatus. A module is an instrument which is separate from other instruments and/or an instrument which can be separated from the other instrument, in particular the laboratory instrument. A laboratory instrument may comprise a connection apparatus, by means of which the module can be connected to the laboratory instrument, in particular by means of a connection which is detachable by the user.

A module may be portable, i.e. transportable by a user. The module can also be securely connected to the laboratory instrument. The modular design offers advantages during the production of laboratory instruments. A portable module offers greater flexibility when using a laboratory instrument.

Preferred embodiments of the access control device and of the laboratory instrument with this access control device are mentioned within the description of the present invention or can be gathered therefrom.

The access control device is preferably configured to control the request of the at least one further user in respect of logging onto the access control device, in particular to control the access to at least one function of the laboratory instrument, in particular to grant the request (access granted) or to reject the request (access denied), during the session of the first user.

The access control device is an apparatus configured for data processing. It serves for access control. The access control device comprises a control apparatus. The control apparatus is embodied for data processing. In particular, the control apparatus is an electronic control apparatus. It preferably has a data processing apparatus which, in particular, is electronic.

The data processing apparatus preferably comprises a computer unit, in particular a CPU, furthermore preferably at least one data storage apparatus, in particular for temporary and/or permanent storage of data. The data processing apparatus is preferably embodied to establish one or more first data connections to one or more user interface apparatuses, which can, in particular, be components of the configuration control device, of the access control device and/or of the laboratory instrument, by means of the first interface apparatus; preferably to establish a second data connection to the laboratory instrument via the second interface apparatus; and preferably to control access permissions for the access of users via the user interface apparatuses and the first and second data connections to functions of the laboratory instrument; wherein, preferably, the access permissions can be controlled in such a way that simultaneous access (being logged on) of a first and at least one further user occurs with in each case separately assigned access permissions to functions of the laboratory instrument.

An interface apparatus serves for connecting two apparatuses which can each process, in particular transmit and/or receive, signals, in particular information, in particular data. An interface apparatus can contain at least one hardware interface and/or at least one software interface.

Hardware interfaces are, in particular, interfaces between electrically operating units in accordance with the usual understanding in electrical engineering and electronics. Presently, the phrase "hardware interface" in particular also denotes the connection components between at least two electrically operating units themselves, i.e., in particular, all constituents which enable this connection, e.g. integrated circuits, electronics and lines, by means of which electrical signals are transmitted between the at least two electrically operating units. In particular, these two electrically operating units can be a laboratory instrument and an external data processing apparatus or two laboratory instruments, or two electrically operating units, within a laboratory instrument. A hardware interface need not, but can, comprise a detachable connection apparatus for releasing and/or re-establishing this connection, in particular at least one connector.

Software interfaces, in particular software-side data interfaces, are, in particular, logical connection points in an information management system, in particular a software system: they enable and regulate the interchange of commands and data between various processes and components. Software interfaces may be data-oriented interfaces used for communication purposes only. In this case, the software interface merely contains information which is interchanged between involved system parts.

The access control device is preferably configured to control the access permissions by virtue of the control apparatus using a data connection to a database for access permissions. The database for access permissions is preferably stored in at least one, preferably in exactly one, storage apparatus for access permissions. The at least one storage apparatus for access permissions can be disposed in the access control device and/or it can be disposed in an external data processing apparatus. "External" means that the instrument, in this case the data processing apparatus, is not a constituent of the device in question, in this case the access control device. The database for access permissions can be stored centrally, but it can also be stored in a plurality of storage apparatuses which can each have some of the data in the database or else have a copy of the data in the database.

An—in particular external—data processing apparatus can be a computer, in particular a server, or can comprise a computer, in particular a server, which is configured for establishing a data connection to more than one access control device and/or to more than one laboratory instrument. An—in particular external—data processing apparatus can comprise a computer or microprocessor. A server is, in particular, a computer, the hardware of which is preferably tuned to server applications. An external data processing apparatus can be a mobile data processing apparatus, which is configured for establishing a wireless data connection, in particular a data connection via a restricted computer network or a world-wide computer network. A computer network is a combination of various technical, primarily independent, electronic systems (in particular computers, but also sensors, actuators, agents and/or other radio components, etc.), which combination enables the communication between the individual systems.

The access control device can comprise a communication apparatus for establishing a data connection to an external data processing apparatus, in particular via the first, second or another interface apparatus of the access control device. The access control device is preferably embodied to establish the access permissions using the data connection to the external data processing apparatus,
in particular via the first, second or another interface apparatus of the access control device. The external data processing apparatus preferably comprises at least part, or all of, the database for access permissions.

The access control device, in particular a control apparatus of the access control device, is preferably configured to control authorizations and/or access permissions for the access of users via the user interface apparatuses and the first and second data connections to functions of the laboratory instrument. As a result of this, a user-dependent use of the laboratory instrument is possible, which is controlled depending on the respectively allocated access permissions. In particular, simultaneous use of the laboratory instrument by at least a first and at least a second user is made possible.

The access control device performs the access control. The phrase "access control" denotes, in particular, methods for managing the requests for resources and/or data, which are managed by an information management system and which are handled for managing the decisions as to how the request is handled, in particular whether or not access is granted and/or in what manner the access is or is not granted. In particular, the information management system can be an operating system which is executed on the access control device. If the user of an information management system wishes to perform a specific operation on a specific resource and/or with specific data, the access control device makes a decision as to whether this request should in actual fact be granted or whether it should be denied. An access control decision (yes/no) relates to, in particular, an access control triple consisting of "subject", "object" and "operation".

In particular, an active entity of a system, wishing to perform a specific operation on a specific object, is referred to as a subject. In this context, an entity denotes a uniquely determinable unit, relating to which information is to be stored and/or processed. The unit may be material or immaterial, concrete or abstract. Subjects are, in particular, human users of an information management system or computer programs which are used by human users for completing tasks. A subject may also be a group of users, e.g. laboratory worker, servicing technician, administrator. Accordingly, the group combines a plurality of individual subjects.

A user may represent an individual, or a group of a plurality of individuals, or a class of individuals, which were selected in accordance with a class rule or role rule.

The access control device can preferably distinguish between the at least one first user and the at least one second user. A user is preferably uniquely identified by the access control device. To this end, the access control device preferably processes identification data. The access control device is preferably embodied to authenticate the requesting user, i.e. to perform a verification method, by means of which the authenticity of the requesting user is checked and the user is authenticated if the verification is positive. By way of example, authentication data contain a login text and a password text or a data set for facial recognition or for an iris scan or for a fingerprint scan, etc. Furthermore, authentication can be performed by means of an RFID chip or NFC chip, or via gesture identification. In particular, an authentication may be performed in situ by means of direct access to the laboratory instrument or the access control device thereof, or by means of remote access.

The access control device preferably comprises an information management system, by means of which the access control is realized. The information management system is preferably an operating system of a laboratory instrument and/or of the access control device thereof, by means of which the access control device and/or the laboratory instrument are operated.

The access control device is preferably embodied to log the requesting user, in particular a plurality of requesting users, in particular the at least one first user and the at least one second user, onto the access control device, in particular onto the information management system of the access control device. The log-on process is also referred to as logging in. The successfully logged-on user preferably receives predetermined authorizations and/or access permissions. The user himself can cancel being logged-on or this can be cancelled by other conditions, for example by the instrument-controlled logging-off of the user, in particular if a maximum logged-on time, during which the user was logged-on, without interruption, via the access control device is exceeded, or after a predetermined time of inactivity, or depending on the time of the end of the treatment performed by the user or due to individual process programming. Cancelling of logging on preferably means that the authorization granted during the log-on is revoked.

Logging into the information management system is preferably brought about by virtue of the user being authenticated. After authentication, the user obtains, for logging-in purposes, a personalized access to the information management system, with authorizations and/or access permissions, which are established by means of the database for access permissions. A session starts with the login and it is terminated by logging out, which is also referred to as logging off.

The access control device is preferably embodied to release the use of, i.e. authorize the authenticated user to use, the authorizations, operations and objects on the laboratory instrument or the functions and services of the laboratory instrument, which comprises the access control device, as a function of the predetermined access permissions. The access control device is preferably software controlled, in particular program controlled. LDAP (Lightweight Directory Access Protocol) is preferably used as application protocol when implementing the software functions.

During access or attempted access, an object refers to, in particular, a passive entity on which an operation is to be performed. Objects are also referred to as "resources". Objects may be e.g.: data or data collections, i.e. files, data objects in databases, e.g. tables or columns, services or functions, in particular those services or functions which can be performed by the access control device and/or the laboratory instrument. By way of example, such services may denote the making available of a calendar database, wherein this use may provide the display of calendar dates, the read permissions and/or write permissions on the calendar database. By way of example, such services and functions may denote a notification function, by means of which it is possible to send notifications to the users, which notifications may, in particular, contain information about the availability of the laboratory instrument during a specific calendar time period. In particular, making it possible for treatment to be performed, which, in particular may contain the granting of the access permissions required for this, would also be such a function. By way of example, a function may be the switching-on of the UV illumination of the laboratory instrument or the opening of a housing door of a laboratory instrument housing.

Processes carried out on an object are referred to as operations. In particular, operations can be functions, in particular functions of the access control device or of the laboratory instrument. A plurality of functions can be performed on one object. If the object is a file, possible operations are writing, reading, adding, modifying, copying or deleting data. If the object is a service or a function, performing may be the only possible operation. The number of possible operations depends on the type of the object. The number of operations which can be performed by individual subjects on the same object may differ.

A specific object in combination with the specific operation is, in particular, referred to as an authorization. By way of example, a "read authorization" can be understood to be the combination of the operation "read" with the object "file", while e.g. an "execution authorization" can be understood to be the operation "execute" with the object "function".

In particular, the access control can be formulated as a permission function, formally described by permission_for(subject, object, operation)→(yes, no)

If this function is applied to the triple of parameters (subject, object, operation), the permission function returns either "yes" (access granted) or "no" (access denied).

In this permission function, it is also possible to provide a further input parameter which supplies a further condition for the access decision. By way of example, this condition can denote the purpose for which a specific access should take place. Furthermore, it is possible that the permission function returns not—or not only—the yes/no decision about the access permission, but also a condition (also referred to as "obligation"), as a function of which a decision is made about the access permission. In particular, this allows "permission with conditions" to be defined. In particular, such an obligation is already satisfied before the access or access attempt, but may also be satisfied during— or after—the access or the operation to be permitted.

The access control can take place in accordance with one or more specific data models. One such specific data model is, in particular, the access control model (ACM). In particular, the access control may comprise a so-called reference monitor. In particular, this component should be understood to be the functional core of the access control device. The reference monitor fulfils the function of deciding whether the access to an object, as desired by a subject, is granted. The access control device may preferably not release any access to a resource of the laboratory instrument without the reference monitor being used. The reference monitor preferably also satisfies the function of recording access attempts that took place.

The database about access permissions preferably contains information in the form of data about which operations are available for an object, in particular as a function of a specific time or time period. In particular, this renders it possible to set whether the access to the at least one treatment apparatus is granted to a user at a specific time and/or during a specific period of time, in particular whether the permission for starting on modifying a treatment on the laboratory instrument has been allocated at a specific time or in a specific time period, wherein the laboratory instrument is or can be connected to the access control device by means of the second data connection.

The database about access permissions preferably contains information in the form of data relating to which authorizations can be allocated to the requesting user, in particular as a function of possible permissions due to belonging to a group and/or belonging to a role.

The access control is preferably configured in accordance with one, or else in accordance with more, of the known basic forms DAC ("Discretionary Access Control"), MAC ("Mandatory Access Control") or RBAC ("Role-Based Access Control"), with RBAC being particularly preferred. The RBAC model provides for individual subjects not to be assigned permissions directly, but rather indirectly by means of so-called "roles". A possible standard of the RBAC model, which can be applied within the scope of designing the access control device, is described in detail in US standard ANSI INCITS 359-2004. The access control device may be embodied at least partly as a RBAC model, in particular at least partly in accordance with the aforementioned US standard.

Preferably, the access control provides the use of at least one role, preferably of a plurality of roles, wherein, in particular, permissions are in each case combined within the role. The at least one role is preferably stored in the database for access permissions. In particular, a role is suitably adapted to a responsibility or a problem description within the scope of using a laboratory instrument, in particular within the business using the laboratory instrument and/or in the business which fulfils a servicing contract relating to the laboratory instrument by virtue of e.g. performing diagnostic functions on the laboratory instrument, and/or in the manufacturer of the laboratory instrument, which e.g. transmits firmware updates, calibrations or information about the laboratory instrument and/or the accessories thereof directly to the laboratory instrument via the access control device. In particular, such roles can combine permissions. Instead of storing a set of individual rights for each user, the latter can be assigned at least one role. The role assignment is particularly reliable in terms of the implementation and requires relatively little outlay, in particular management outlay when establishing and storing permissions.

The access control preferably provides for at least two, preferably a plurality of, roles. Possible roles are, in particular, administrator ("Admin"), maintenance, normal laboratory user ("LabUser"), inexperienced laboratory user ("Inexperienced"), manager. Such roles enable a secure and efficient access control. The use of a laboratory instrument provided with the access control device is safe and efficient. This prevents, in a simple manner, a user, for example due to lack of qualification, from performing certain operations on the laboratory instrument which could possibly lead to damage or inefficient use of the laboratory instrument or to increased costs during operation, e.g. due to excessive use of consumables used for a treatment.

The access control preferably provides at least one role, or more than one role, which can be assigned simultaneously to a user. Therefore, an individual can, for example, obtain access as administrator or as normal laboratory user, depending on a further condition. The user can preferably decide himself the role in which he obtains access to the laboratory instrument. However, it is also possible that the user does not decide this himself, but that this is decided by the access control device. This condition may be the data record used for authentication purposes, in particular the used password, or it may depend on a parameter of the laboratory instrument, in particular on an operating parameter of the laboratory instrument, e.g. an operating parameter which characterizes an error state of the laboratory instrument.

The control apparatus of the access control device is preferably configured to allow more than one user to be logged on simultaneously on the access control device in order to have authorizations and/or access permissions assigned to them. Such an access control device for simultaneous use of a laboratory instrument constitutes an efficient solution for increasing the productivity in a laboratory.

Preferably, the access control device, in particular the control apparatus of the access control device, is configured in such a way that an additional check is carried out as to whether at least one further predetermined condition is satisfied during the log on at the user interface apparatus and the access permissions for access to the laboratory instrument via the second user interface apparatus are only assigned if the at least one further predetermined condition is also satisfied.

Preferably, the configuration control device, in particular the control apparatus of the configuration control device, is configured in such a way that an additional check is carried out as to whether at least one further predetermined condition is satisfied during the log on at the user interface apparatus and a user-dependent control of the display on a user interface is only used if the at least one further predetermined condition is also satisfied.

This further predetermined condition or these further predetermined conditions can depend on the role of the user, on the status of the laboratory instrument and/or on the type of user interface apparatus, which the laboratory instrument identified when the connection to the laboratory instrument was established.

This further predetermined condition or these further predetermined conditions may, in particular, be dependent on the use case. Similar conditions can, in general, be taken into account by the access control device when a decision is made about the allocation of authorizations and/or access permissions to a logging-on or logged-on user.

Possible use cases are, for example, in each case preferably, the observation of the laboratory instrument by means of a remote data connection ("remote monitoring"), the control of the laboratory instrument by means of a remote data connection ("remote control"), the use of a booking schedule for time-dependent planning of the use of the laboratory instrument by a plurality of users ("booking schedule"), the pre-programming of a treatment, in particular of a program-controlled treatment, in particular by process programming ("pre-programming") or the remote access by a service technician ("remote service access"). The condition can furthermore take into account the role of the user and/or the operating state of the laboratory instrument. The operating state of the laboratory instrument can, in particular, be an idle state, i.e. a state without, in particular, a running treatment, in which, however, the laboratory instrument can be ready, in particular, for the log on of a user and/or for carrying out a treatment. The operating state of the laboratory instrument can, in particular, be a state in which a treatment is or was programmed and/or the treatment was prepared and is just about to be carried out. The operating state of the laboratory instrument can, in particular, be a state in which the treatment was already started and is running, or a state in which the treatment was stopped or a state in which the booking schedule has a booking entry for the treatment by a user, wherein a distinction can be made as to whether or not this user is logged on. The operating state of the laboratory instrument can, in particular, be an energy saving state ("standby" mode) of the laboratory instrument. Further examples of possible or preferred embodiments of such authorizations as a function of the aforementioned conditions are found in "Appendix 1" of the description.

Preferably, the access control device, in particular the control apparatus of the access control device, is configured in such a way that, in particular if a further condition is satisfied, information about the operating state of the laboratory instrument, measured values or settings and programs of the laboratory instrument which can be influenced by the user are transmitted to the second user interface apparatus via the interface apparatus. In particular, this condition may be that a user has requested this information transfer at the access control device. Preferably, the access control device, in particular the control apparatus of the access control device, is configured in such a way that, if this condition is satisfied, information about the operating state of the laboratory instrument, measured values or settings and programs of the laboratory instrument which can be influenced by the user are transmitted to the second user interface apparatus via the interface apparatus.

Preferably, the access control device, in particular the control apparatus of the access control device, is configured in such a way that the settings which can be influenced by the user contain at least one program parameter for the program-controlled treatment of a laboratory sample, which, in particular, is controlled by means of a process program.

Preferably, the control apparatus of the access control device and/or the control apparatus of the laboratory instrument comprises a storage apparatus in which user qualification data are stored, which are assigned each user of the laboratory instrument qualification in the form of at least one qualification value or certificate. Preferably, the access control device, in particular the control apparatus of the access control device, is configured in such a way that the authorizations and/or access permissions are granted to a user, in particular, the latter is assigned a role, as a function of his qualifications. As a result of this, users may use the laboratory instrument in accordance with their qualification and, in particular, inexperienced users are not overwhelmed. As a result, the productivity and operational safety during use of the laboratory instrument are increased.

Preferably, the control apparatus of the access control device and/or the control apparatus of the laboratory instrument are embodied to carry out a qualification method for at least one user, in which the at least one user runs through a qualification exam, which is carried out and evaluated by the control apparatus, and wherein the qualification method in particular provides for the data entered by the at least one user as a response to specific questions, in particular to questions related to technical details of a laboratory instrument, or to the professional treatment of laboratory samples, in general or in dependence on specific laboratory applications, to be evaluated, and in particular provides for the at least one user to be assigned a qualification, in particular in accordance with a comparison table or a computational prescription, as a function of the result of this evaluation. Such a qualification method carried out on the access control device or on the laboratory instrument is particularly practically relevant and therefore efficient.

Preferably, the control apparatus of the access control device and/or the control apparatus of the laboratory instrument are embodied, by means of the access control device, to grant and/or withdraw certain access permissions to functions of the laboratory machine to or from the user, depending on his qualification.

Preferably, the control apparatus of the access control device and/or the control apparatus of the laboratory instrument are embodied to display to the user, depending on his qualification, at least one graphical user interface, which corresponds to the qualification, on the display of the user interface apparatus and/or, in particular, to make available or not make available certain assistance programs or auxiliary information.

Preferably, the control apparatus of the access control device and/or the control apparatus of the laboratory instrument comprises a timer, in particular a clock, and, in particular, a booking apparatus, which comprises a storage apparatus which stores booking data, which, in particular, contain at least one booking data record or a plurality of booking data records, which describe at least one booking schedule, in particular individually for each treatment apparatus.

A booking data record contains, in particular, at least one of the items of information, in particular, which user, in particular at what time, carries out, has carried out or will carry out, in particular, which treatment of samples, in particular by means of which the laboratory instrument. The booking data preferably contain information about the bookings accepted by the booking apparatus, which bookings were in fact confirmed after comparison with the free capacities present in the booking schedule and were recorded in the booking schedule. However, the booking data may also contain booking requests, which the booking apparatus can recheck, in particular even at a later time after the request was placed, and possibly accept at a later date, for example if an earlier entry in the reservation schedule was subsequently cancelled. The reservation data record preferably also contains information about what type of treatment is in each case planned on the laboratory instrument, what specific period of time or what duration of occupying the laboratory instrument is envisaged in the process and/or information about the process program used, and preferably contains, in particular, at least one program parameter or control parameter.

Preferably, the access control device is configured to transmit to a user upon request at least one item of information about the booking schedule, in particular to transmit the whole or part of the booking schedule or to transmit at least one change in the booking schedule. Preferably, the access control device is configured to transmit a notification automatically to a user, depending on at least one condition. This condition could be the change in the reservation schedule of a laboratory instrument, in particular in relation to the availability of a date for carrying out a treatment, in particular the release or cancelling of a date.

The "type of treatment" is, in particular, predetermined by the program parameters characterizing treatment. Such program parameters are, in particular, used by the control apparatus to generate a process program. In particular, a process program is a control code for controlling the treatment by means of control parameters. In particular, the control parameters are generated by the control apparatus, in particular by a control program running on the control apparatus, e.g. an operating system, while using the program parameters. The treatment of a sample is carried out, in particular, by virtue of a process program being executed by the control apparatus.

A "type of treatment" means a process, namely a type of application (e.g. "MagSep Blood gDNA", "Compose Mastermix" etc.). In a preferred configuration of the laboratory instrument as laboratory machine, the user initially selects a desired application, i.e. a "type of treatment", by virtue of selecting an application, in particular on the touchscreen of an instrument. This application, which is also referred to as "process", is, in particular, assigned to a program module which, in particular, may be a constituent of the control program. In particular, at least one program parameter is queried by the user by means of the program module. A program module generates, in particular, a process program on the basis of the at least one program parameter selected by the user.

Preferably, the control apparatus of the access control device and/or the control apparatus of the laboratory instrument is embodied to store booking data in the storage apparatus of the booking apparatus.

Preferably, the control apparatus of the access control device and/or the control apparatus of the laboratory instrument is configured to record the booking data record entered by the user into the laboratory instrument, in particular by means of the user interface apparatus or a portable or mobile user interface apparatus.

Preferably, the control apparatus of the access control device and/or the control apparatus of the laboratory instrument is embodied to compare the booking data record entered by the user with booking data already stored in the storage apparatus of the user interface apparatus.

Preferably, the control apparatus of the access control device and/or the control apparatus of the laboratory instrument is configured to store at least one, some or all booking data records, entered by at least one user, in the storage apparatus.

Preferably, the control apparatus of the access control device and/or the control apparatus of the laboratory instrument is embodied to evaluate some or all booking data records, entered by at least one user and stored in the storage apparatus, in accordance with an evaluation method stored in the storage apparatus and to create the schedule according to at least one criterion by virtue of the booking data records being sorted in accordance with the at least one criterion of a sort method stored in the control apparatus.

Preferably, the control apparatus of the access control device and/or the control apparatus of the laboratory instrument is embodied to assign the at least one booking data record a priority by means of an evaluation method, which priority is established in accordance with at least one criterion.

The criterion can, in particular, be represented by a data table stored in the control apparatus, in which data table e.g. the priority is related to at least one other parameter, wherein this other parameter may characterize e.g. the user or a user group, or the classification of a treatment in accordance to a list of relevance (e.g. from important to unimportant, expensive to cost-effective, etc.).

Preferably, the control apparatus of the access control device and/or the control apparatus of the laboratory instrument is embodied in such a way that the sort method sorts at least two booking data records in accordance with at least one criterion in order, in particular, to create a schedule which uses other time data than what is provided for in the booking data records of the users.

The criterion can be selected in accordance with the definitions in the evaluation method. Preferably, in order to realize a preferred criterion, the control apparatus is embodied to sort the booking data records under the aspect of a resource being optimized.

By way of example, the resource can be the time; in particular, a minimization of the waiting times can be sought after, a user in each case experiencing said waiting times as the difference between the start time, as desired by said user, and the start time, assigned by the laboratory instrument after evaluation and sort, for the experiment of said user, i.e. the treatment desired by said user. The minimization of the passive time, during which a laboratory instrument is not used, may also be sought after. In particular, it is also possible to plan intermediate servicing, cleaning and/or sterilization procedures, during which e.g. at least one workspace of at least one laboratory instrument or laboratory machine is prepared, in particular prepared manually and/or automatically, and/or cleaned and/or sterilized.

The resource may also be the energy which, as a function of the sequence of treatments, is possibly consumed to a different extent over different and successive ones of said treatments.

The resource may be a consumable, in particular a substance, e.g. a cleaner, or specific transport containers, e.g. pipette tips, or storage containers, e.g. microtiter plates, which, as a function of the sequence of treatments, are consumed to a different extent over various and successively carried out ones of said treatments. The same processes are possibly used in treatments planned by different users, and so it may be efficient to sort bookings on the basis of the processes. By way of example, it is conceivable that a specific substance and/or a specific consumable and/or a specific tool is used in a plurality of processes planned by different (or the same) user(s). Then, it may be particularly efficient to store this substance or this consumable or this tool in the laboratory instrument such that some transport processes become superfluous, as a result of which time and, optionally, the resource itself are saved, which resources often need to be stored under sterile conditions. By way of example, it would also be possible for two treatments, provided temporally in succession in the booking schedule, to be able to share specific consumables. By way of example, one and the same storage container could be used in both treatments, and therefore it is efficient to use the storage container for the second treatment after completion of the first treatment instead of disposing of the first storage container at the end of the first treatment and using a further storage container at the beginning of the second treatment. As a result, it is possible to save material and time in many situations.

The resource can also be the plurality of laboratory instruments, on which the bookings occurring during a booking period of time are to be distributed automatically in accordance with the plurality of booking data records from a plurality of users in order to obtain an optimal use of the parks of laboratory instruments available in a laboratory. In particular, there may be experiments which require the synchronized use of more than one laboratory instrument. The resource may therefore consist of using a plurality of laboratory instruments optimally in time, in particular taking into account at least one experiment or a plurality of experiments which may each require different laboratory instruments.

By way of example, it is possible that a higher ranked role, e.g. an "administrator", is able to delete or move booking entries scheduled in the booking schedule, for example because an (external) service technician wishes/needs to service the treatment apparatus(es) on said date or because of other aforementioned reasons. Particularly from the view of the customer, an action without consultation is not preferred, rather a note to the user(s) of the booked one or more treatment apparatuses to the effect that the use of the treatment apparatus needs to be moved to a later date is preferable. In this context, proposing a suitable alternative time may also be expedient. The control apparatus is preferably embodied to emit such a notification via the user interface apparatus of the relevant user, in particular by using a remote data connection.

To the extent that a treatment apparatus is in strong demand, a booking mechanism, which is designed as a FIFO list (FIFO—first in, first out) and which in turn is used for informing the top-most user the moment the treatment apparatus becomes unoccupied or when said treatment apparatus will not be occupied during a selected future period of time, is particularly suitable. This information then preferably also comprises the timeframe for which the treatment apparatus is available. The topmost user would then receive the priority to occupy the treatment apparatus for a defined period of time. If he does not do this, the user is removed from the list and the option for occupation is transferred to the next user on the list, etc.

The term "instrument-controlled treatment" means that the treatment of the at least one laboratory sample is at least partly controlled, in particular performed, by the laboratory instrument. To the extent that the treatment is controlled and/or carried out by the laboratory instrument, said treatment in this respect is, in particular, not controlled and/or performed by the user, in particular not controlled and/or performed manually by the user.

An instrument-controlled treatment is furthermore preferably understood to mean that the treatment is at least partly controlled, in particular performed, by the laboratory instrument as a function of at least one user input. The user input may occur prior to the start of the treatment and/or during the treatment. The user input preferably occurs using a user interface apparatus, which is preferably a component of the laboratory instrument or which is provided separately from the laboratory instrument and signal connected to the control apparatus of the laboratory instrument and/or to the control apparatus of the access control device. The user input serves, in particular, for entering at least one parameter, the value of which influences and/or controls the treatment. This parameter can, in particular, be a program parameter.

The "instrument-controlled treatment" denotes, in particular, the at least partly automated treatment. In the case of the partly automated treatment, it is possible, in particular, for the treatment to be performed in such a way that, after the treatment has started and before the treatment is complete, there is at least one user input, by means of which the user can influence current treatment, in particular by virtue of said user e.g. responding to an automatic query brought about by means of a user interface apparatus of the laboratory instrument, in particular by virtue of confirming or denying this or undertaking other inputs. In the case of the partly automated treatment, it is possible, in particular, for the treatment to have a plurality of treatment steps which, in particular, are performed automatically and successively in time and which have at least one treatment step that requires a user input, which, in particular, is brought about via a user interface apparatus.

An instrument-controlled treatment is preferably a program-controlled treatment, i.e. a treatment controlled by a program. A program-controlled treatment of a sample should be understood to mean that the process of treatment substantially takes place by working through a plurality or multiplicity of program steps. Preferably, the program-controlled treatment takes place using at least one program parameter, in particular at least one program parameter selected by the user. A parameter selected by a user is also referred to as a user parameter. The program-controlled treatment preferably takes place with the aid of a digital data processing apparatus which, in particular, may be a component of the control apparatus of the laboratory instrument. The data processing apparatus can comprise at least one processor, i.e. a CPU, and/or at least one microprocessor. The program-controlled treatment is preferably controlled and/or performed in accordance with the prescriptions of a program, in particular a control program. In particular, substantially no user activity is required in the case of a program-controlled treatment, at least after acquisition of the program parameters required from the user.

A program parameter is understood to mean a variable which can be set in a predetermined manner within a program or sub-program and is valid for at least one execution (call) of the program or sub-program. The program parameter is set, e.g. by the user, and controls the program or sub-program and causes a data output as a function of this program parameter. In particular, the program parameter influences and/or controls the control of the instrument, and/or the data output by the program control said instrument, in particular the control of the treatment by means of the at least one treatment apparatus.

A program parameter may be a program parameter required on the part of the user. A program parameter required on the part of the user is distinguished by the fact that it is required for performing a treatment, in particular for performing a process program. Other program parameters, which are not required on the part of the user, may be derived from the program parameters required on the part of the user or may be made available in a different manner, in particular they may optionally be set by the user. In particular, a program parameter is set by a user by displaying a selection of possible predetermined values from a list of predetermined values stored in the laboratory instrument, wherein the user selects, and therefore sets, the desired parameter from this list. It is also possible for this program parameter to be set by virtue of the user entering the value, e.g. by virtue of entering a numeric number corresponding to the desired value by means of a numeric pad or by virtue of said user increasing or reducing a value continuously or in increments until said value corresponds to the desired value and the value is set thus. Other forms of entry, e.g. by voice control and/or gesture control, are conceivable.

A program is, in particular, understood to mean a computer program. A program is a sequence of statements, in particular consisting of declarations and instructions, enabling a specific functionality, object or problem to be handled and/or solved on a digital data processing system. A program is generally available as software which is used with a digital data processing system. In particular, the program can be available as firmware, in particular as firmware of the control apparatus of the laboratory instrument and/or of the access control device in the case of the present invention. The program is usually available as a program file, often in the form of so-called machine code, which can be executed on a data medium, which program file is loaded into the main memory of the computer of the digital data processing system for execution purposes. The program is processed and therefore executed by the processor(s) of the computer as a sequence of machine commands, i.e. processor commands. In particular, a "computer program" is also understood to mean the source text of the program from which the executable code can be generated in the progress of the control of the laboratory instrument.

As is conventional, a statement denotes a central element of a programming language. Programs of such languages are primarily composed of one or more statements. A statement constitutes a single prescription, formulated within the syntax of a programming language, which prescription is to be executed when working through the program. The syntax of a statement is set by the respective programming language or the specification thereof. In machine-oriented programming, statements are often also referred to as commands.

Statements are usually assignments, control statements (such as branches, loops and conditional statements) and procedural calls. Assertions, declarations, class definitions and function definitions and statements are in part also dependent on the programming language. Thus, the statements of the control program can be configured in a conventional manner.

As is conventional, a program module is understood to be a complete functional unit of software, consisting of a sequence of processing steps and data structures. Here, in particular, the following definitions may apply: the content of a module is often a recurring calculation or handling of data, which needs to be carried out a number of times. Modules offer an encapsulation by separating interface and implementation: the interface of a module defines the data elements which, as input and result of the processing, are required by the module. The implementation contains the actual program code. By way of example, a module is called as a function or sub-program, executes a number of processing steps and, as a result, provides data back to the calling program. A module itself is able to call further modules—thus, a hierarchy of program calls is possible. The data structures and processes set in modules can, when necessary, be inherited and inherited by other modules. Therefore, modules are an essential element in structured and object-oriented programming.

A control program is understood to mean an executable computer program, which preferably controls and/or performs the desired treatment of the at least one sample, in particular as a function of at least one program parameter. This program parameter can be a program parameter influenced and/or set by the user. In particular, the treatment can be controlled by virtue of the control apparatus generating one or more control parameters as a function of the program parameters, by means of which control parameters the at least one treatment apparatus is controlled. The laboratory instrument preferably has an operating system, which can be or comprise a control program. In particular, the control program can denote an operating system of the laboratory instrument or a component of the operating system. The operating system controls the treatment and further operating functions of the laboratory instrument.

In particular, the control program can be signal connected to the access control device and/or can control the access control device. The control apparatus of the access control device can be integrated into the control apparatus of the laboratory instrument or can be embodied separately from this control apparatus. The access control device can be integrated into the control apparatus of the laboratory instrument. The control device of the access control device can be integrated into control device of the laboratory instrument, can be controllable by the control program and/or can, in particular, be integrated into the control program. The control program can control further preferably provided functions of the laboratory instrument, for example an energy-saving function of the laboratory instrument or a communication function for communication with external data processing apparatuses which, in particular, are provided separately from the laboratory instrument and, in particular, are not a component of the laboratory instrument.

A process program is understood to mean a program which determines the specific progress of a treatment, in particular in accordance with a predetermined type of treatment and/or in accordance with a manner set on the part of the user.

The invention furthermore relates to a laboratory instrument for instrument-controlled treatment of at least one laboratory sample, which laboratory instrument comprises at least one treatment apparatus for performing the treatment of the at least one laboratory sample, and an access control device according to the invention.

Preferably, the laboratory instrument comprises a communication apparatus for establishing a remote data connection for data interchange with an external instrument, which likewise comprises a suitable communication apparatus for establishing a remote connection for data interchange with the laboratory machine. Such a communication apparatus can be embodied for establishing a radio connection, in particular a mobile communications connection. The communication apparatus is preferably configured to enable remote access of the user to the laboratory instrument, in particular for selecting or setting of at least one parameter, in particular a parameter which controls a function of the laboratory instrument, in particular the function of performing a treatment.

Preferably, the control apparatus of the access control device or of the laboratory instrument is embodied to provide synchronization data. Preferably, the access control device, in particular the control apparatus of the access control device, is configured in such a way that, if at least one condition is satisfied, information about the operating state of the laboratory instrument, measured values or settings and programs of the laboratory instrument which can be influenced by the user are transmitted to the second user interface apparatus via the interface apparatus. As a result of this information transfer, the laboratory instrument, in particular a treatment running thereon, can continue to be observed and/or controlled by means of the second user interface apparatus. In particular, the use state of the first interface apparatus can be partly or completely copied or cloned in the second user interface apparatus. The information transfer can, in particular, be a synchronization process. The first and second user interface can be synchronized, in particular in this manner. The at least one condition may be that the access of the accessing user is brought about by means of a remote data connection via a (mobile) user interface apparatus and the request of the user is brought about after synchronization. The at least one condition can moreover be the condition a) or b), namely the response to the check whether the logging-on user has already previously, via a first user interface apparatus, a) activated one or more currently executed functions of the laboratory instrument or b) logged on. In cases a) and b), the synchronization would for a user with an active session and/or with currently activated functions on the laboratory instrument, in particular with running treatments which were initiated by the user. However, it is also possible and preferred for a further user to be allowed to carry out synchronization, e.g. in order to perform remote control for the purpose of providing assistance during the current session or treatment or for the purpose of carrying out servicing works, etc.

Preferably, the control apparatus of the access control device is configured to transfer these synchronization data to an—in particular mobile—user interface apparatus. Preferably, these synchronization data are suitable for displaying the information displayed in the display of the user interface apparatus at least partly in an identical manner on the display of the (mobile) user interface apparatus.

The term laboratory instrument denotes, in particular, an instrument which is embodied for instrument-controlled treatment of at least one laboratory sample and which is embodied for use in a laboratory. This laboratory can be, in particular, a chemical, biological, biochemical, medical or forensic laboratory. Such laboratories serve for research and/or analysing laboratory samples, but can also serve for the manufacture of products by means of laboratory samples or the manufacture of laboratory samples.

A laboratory instrument is preferably one of the following laboratory instruments and/or is preferably embodied as at least one of the following laboratory instruments: a laboratory centrifuge, also referred to as "centrifuge" within the scope of the description of the present invention; a thermocycler, also referred to as "cycler" within the scope of the description of the present invention; a laboratory spectral photometer, also referred to as "biospectrometer" within the scope of the description of the present invention; a cell counting instrument, also referred to as "cell counter" within the scope of the description of the present invention, in particular optical counting instruments; a laboratory incubator, also referred to as "incubator" within the scope of the description of the present invention; a laboratory shaker, also referred to as "shaker" within the scope of the description of the present invention; a laboratory mixer, also referred to as "mixing device"; a laboratory freezer, also referred to as "freezer" within the scope of the description of the present invention; a bioreactor, also referred to as fermenter within the scope of the description of the present invention; a safety work bench, in particular biological safety cabinet, also referred to as "biosafety cabinet" within the scope of the description of the present invention; a sample plate reader, also referred to as "plate reader" within the scope of the description of the present invention, in particular "microplate reader"; a laboratory machine for treating fluid samples, in particular a pipetting machine.

A laboratory centrifuge is an instrument which works using inertia. The laboratory centrifuge, in particular the treatment apparatus of the laboratory centrifuge, comprises, in particular, at least one rotor, in which the at least one laboratory sample can be disposed. The at least one rotor is disposed rotatably in at least one centrifuge vessel. The laboratory centrifuge, in particular the treatment apparatus of the laboratory centrifuge, comprises at least one drive apparatus, by means of which the rotation is driven and/or braked. The samples can be disposed in the at least one rotor, preferably in laboratory containers, e.g. sample tubules, which are disposed in suitable holders in the rotor. The laboratory centrifuge, in particular the treatment apparatus of the laboratory centrifuge, preferably comprises at least one heater/cooling apparatus, by means of which the temperature of the at least one sample disposed in the rotor can be controlled and/or regulated. The laboratory centrifuge, in particular the treatment apparatus of the laboratory centrifuge, preferably comprises a timer apparatus, by means of which time parameters of the rotation or temperature settings can be controlled. The functionality is based upon the centrifugal force, which occurs due to a uniform circular motion of the samples to be centrifuged. The centrifugal force is used for substance separation of substances with different densities, which are contained in a sample. A centrifuge can perform a separation method, in which, in particular, the constituents of suspensions, emulsions and/or gas mixtures are separated. The instrument-controlled treatment of the at least one laboratory sample corresponds to a rotational treatment in a laboratory centrifuge, with at least one sample being subjected to said rotational treatment. Possible parameters, in particular program parameters, in particular user parameters, which are used to influence a rotational treatment, define, in particular, a temperature of the laboratory centrifuge, a rotational speed of the laboratory centrifuge, a time parameter of the rotation or a temperature setting and/or at least one progress parameter, which influences or defines the progress, in particular the sequence, of a rotation program consisting of a plurality of rotation steps. The temperature of the laboratory centrifuge can, in particular, be at least one temperature in the interior of the at least one rotor, in particular at least one temperature of at least one sample.

A thermocycler is an instrument that is able, successively in time, to set the temperature of at least one sample to a predetermined temperature and to keep said sample at this temperature level for a predetermined duration. The progress of this temperature control is cyclical. That is to say, a predetermined temperature cycle, i.e. a sequence of at least two temperature levels, is carried out repeatedly. This method serves, in particular, for performing a polymerase chain reaction (PCR). In this context, a thermocycler is sometimes also referred to as a PCR block. A thermocycler, in particular the treatment apparatus of the thermocycler, preferably has a thermoblock. A thermoblock is a sample holder made of a heat-conducting material, usually a metal-containing material or a metal, in particular aluminium or silver. The sample holder comprises a contacting side which is contacted by at least one heater/cooling apparatus of the thermocycler, in particular by a Peltier element. The thermocycler, in particular the treatment apparatus of the thermocycler, comprises a regulation apparatus with at least one control loop, to which the at least one heater/cooling apparatus is assigned as an actuator and at least one temperature measurement apparatus is assigned as a measurement member. The temperature is regulated to a temperature level by means of the controlling system. A cooling body of the thermocycler, in particular of the treatment apparatus of the thermocycler, serves for cooling sections of the thermocycler, in particular for cooling the Peltier elements. The thermocycler, in particular the treatment apparatus of the thermocycler, may comprise further heater and/or cooling elements. The thermocycler, in particular the treatment apparatus of the thermocycler, preferably comprises a timer apparatus, by means of which time parameters for setting the temperature cycle can be controlled. The instrument-controlled treatment of the at least one laboratory sample corresponds to a temperature cycle treatment in a thermocycler, with at least one sample being subjected to said rotational treatment. Possible parameters, in particular program parameters, in particular user parameters, which are used to influence a temperature cycle treatment, define, in particular, the temperature of the temperature level, the duration of a temperature level, the control of further heater and/or cooling elements and/or the number of temperature levels or cycles and/or at least one progress parameter, which influences or defines the progress, in particular the sequence, of a temperature monitoring program consisting of a plurality of steps.

A laboratory spectrophotometer is an instrument which, by illuminating at least one measurement volume of at least one laboratory sample, usually over the whole spectrum of visible light from infrared to ultraviolet, establishes the values of diffuse reflection. Diffuse reflection refers to the situation in which a measurement volume absorbs part of the light spectrum and transmits part of the spectrum (transparent media) or reflects it (opaque media). The laboratory spectrophotometer is used, in particular, to measure the absorptivity of a sample as a function of the light wavelength. Moreover, it is possible, in particular, to extend the field of application of the laboratory spectrophotometer by means of various modules. By way of example, it is conceivable to dispose a fluorescence module for measuring fluorescence or a temperature-control module for controlling the temperature of the sample in the spectrometer. The measured absorption spectrum contains, in particular, the light intensities measured at specific wavelengths. The absorption spectrum is typical of the laboratory sample or the substance contained therein or the substances. This can be used for qualitative analysis of the laboratory sample. If the liquid sample or the substance dissolved therein is known, the concentration of the dissolved substance can be established by measuring the absorption. This can be used for quantitative analysis of the laboratory sample. The laboratory spectrophotometer, in particular the treatment apparatus of the laboratory spectrophotometer, preferably comprises at least one light source, preferably at least one timer, preferably at least one photodetector. The instrument-controlled treatment of the at least one laboratory sample corresponds to a light and measurement treatment in a laboratory spectrophotometer, with at least one sample being subjected to said treatment. Possible parameters, in particular program parameters, in particular user parameters, which are used to influence a light and measurement treatment, define, in particular, the optical light spectrum, by means of which the at least one sample is irradiated and/or at least one progress parameter, which influences or defines the progress, in particular the sequence, of a light and measurement treatment program consisting of a plurality of steps.

A cell counting instrument serves for counting biological cells or particles which are contained in the laboratory sample. There are different physical principles which can be used to count cells, in particular optical methods, in which the laboratory sample to be measured is disposed in a counting chamber, there is additional illumination, particularly in the case of automatically operating ones, and an image of the cells or particles disposed in the counting chamber is acquired and evaluated. A further established method lies in measuring the impedance: a cell counting instrument embodied as a Coulter counter guides the laboratory sample containing the cells through an aperture ("measurement port"). Each passage of a cell through the aperture is detected electrically as a countable event. Optical cell counting instruments, in particular the treatment apparatus of the cell counting instrument, preferably comprise, depending on the embodiment, at least one light source, at least one image acquisition unit and at least one image evaluation unit*, and additionally, inter alia, a positioning apparatus. The instrument-controlled treatment of the at least one laboratory sample corresponds e.g. to a light and measurement treatment in the case of an optical cell counting instrument, a pumping and measurement treatment in the case of an instrument operating according to the Coulter principle, to which treatment the at least one sample is subjected. Possible parameters, in particular program parameters, in particular user parameters, which are used to influence a light and measurement treatment or the pumping and measurement treatment, define, in particular, the light intensity of the light source, by means of which the at least one sample is irradiated and/or at least one progress parameter, which influences or defines the progress, in particular the sequence, of a light and measurement treatment program or the pumping and measurement treatment program consisting of a plurality of steps. Moreover, in the case of optical counting instruments, the algorithms necessary for the image evaluation, the sequence and parameterization thereof are decisive for the significance of the measurement result ???. Optical measurement instruments, but also Coulter counters, often use counting chambers for single use ("consumables"); these are plastic articles in the style of conventional Neubauer counting chambers or, in the case of Coulter counters, "lab-on-a-chip"-like disposable counting chambers. However, there are also instruments which operate without these consumables (e.g. "CASY").

A laboratory incubator is an instrument by means of which controlled climatic conditions for various biological development and growth processes can be set up and maintained. It serves to set up and maintain a microclimate with regulated gas and/or humidity and/or temperature conditions in an incubator space, wherein this treatment may be dependent on time. The laboratory incubator, in particular the treatment apparatus of the laboratory incubator, comprises, in particular, a timer, in particular a timer switch, a heater/cooling apparatus and preferably a setting for regulating the substitute gas supplied to the incubator space, in particular fresh air, a setting apparatus for the composition of the gas in the incubator space of the laboratory incubator, in particular for setting the $CO_2$ and/or $O_2$ content of the gas and/or a setting apparatus for setting the humidity in the incubator space of the laboratory incubator. The laboratory incubator, in particular the treatment apparatus of the laboratory incubator, comprises, in particular, the incubator space, furthermore preferably a regulation apparatus with at least one control loop, to which at least one heater/cooling apparatus is assigned as an actuator and at least one temperature measurement apparatus is assigned as a measurement member. The temperature can be regulated in the incubator by means of the controlling system. $CO_2$ incubators serve, in particular, for cultivating animal or human cells. Incubators may have turning devices for turning the at least one laboratory sample and/or a shaker apparatus for shaking or moving the at least one laboratory sample. The instrument-controlled treatment of the at least one laboratory sample corresponds to a climate treatment in a laboratory incubator, with at least one sample being subjected to said treatment. Possible parameters, in particular program parameters, in particular user parameters, which are used to influence a climate treatment, define, in particular, the temperature of the incubator space, in which the at least one sample is incubated, the $O_2$ and/or $CO_2$ partial pressure in the incubator interior, the humidity in the incubator interior and/or at least one progress parameter, which influences or defines the progress, in particular the sequence, of a incubation treatment program consisting of a plurality of steps.

A laboratory shaker serves for moving a laboratory sample, in particular for mixing a laboratory sample comprising a plurality of constituents. There are different embodiments of laboratory shakers, in particular overhead shakers or flatbed shakers. Laboratory shakers can comprise a temperature control function for controlling the temperature of at least one laboratory sample and can, in particular, comprise an incubator function for incubating the at least one laboratory sample in controlled climatic conditions. Laboratory shakers, in particular the treatment apparatus thereof, can, in particular, be configured to perform an oscillating motion. Laboratory shakers, in particular the treatment apparatus thereof, comprise, in particular, a drive for driving the motion, comprise, in particular, a timer apparatus, by means of which time parameters of the setting of the shaker treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a shaker treatment in a laboratory shaker, with at least one sample being subjected to said treatment. Possible parameters, in particular program parameters, in particular user parameters, which are used to influence a shaker treatment, define, in particular, the movement intensity, in particular the movement frequency in the case of an oscillating drive, a time period during the shaker treatment and/or at least one progress parameter, which influences or defines the progress, in particular the sequence, of a shaker treatment program consisting of a plurality of steps.

A laboratory mixer, also referred to as "mixing device", serves like the laboratory shaker for moving a laboratory sample, in particular for mixing a laboratory sample comprising a plurality of constituents. Compared to a laboratory shaker, a laboratory mixer enables movements with higher frequencies, in particular with higher rotational speeds. Laboratory mixers, in particular the treatment apparatus thereof, can, in particular, be configured to perform an oscillating motion. Laboratory mixers, in particular the treatment apparatus thereof, comprise, in particular, a drive for driving the motion, comprise, in particular, a timer apparatus, by means of which time parameters of the setting of the mixer treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a mixer treatment in a laboratory mixer, with at least one sample being subjected to said treatment. Possible parameters, in particular program parameters, in particular user parameters, which are used to influence a mixer treatment, define, in particular, the movement intensity, in particular the movement frequency in the case of an oscillating drive, a time period during the mixer treatment and/or at least one progress parameter, which influences or defines the progress, in particular the sequence, of a mixer treatment program consisting of a plurality of steps.

A laboratory freezer serves for storing at least one laboratory sample in a freezer room at regulated temperatures, in particular in the freezer range from −18° C. to −50° C. or in the ultra-freezer range from −50° C. to −90° C. In particular, a laboratory freezer is not a refrigerator, which can be used for cooling at temperatures in the range from 0° C. to 10° C. or from −10° C. to 10° C. in particular. The laboratory freezer, in particular the treatment apparatus of the laboratory freezer, comprises, in particular, at least one cooling apparatus and at least one regulation apparatus with at least one control loop, to which at least one cooling apparatus is assigned as an actuator and at least one temperature measurement apparatus is assigned as a measurement member. A laboratory freezer, in particular the treatment apparatus of the laboratory freezer, comprises, in particular, a monitoring measurement instrument for measuring the temperature and/or in particular at least one alarm apparatus, by means of which an alarm signal is emitted if the temperature measured in the freezer space departs from a permitted temperature range.

A laboratory freezer, in particular the treatment apparatus of the laboratory freezer, can, in particular, comprise an information reader for reading information. This information can be contained in an information medium which can be connected to an article. This article can, in particular, be a sample container which can contain at least one laboratory sample. The information medium can, in particular, comprise an RFID chip or other identification features, such as e.g. a barcode, a data matrix code, a QR code, which can be read by suitable methods. The instrument-controlled treatment of the at least one laboratory sample corresponds to a low-temperature treatment in a laboratory freezer, with at least one sample being subjected to said treatment. Possible parameters, in particular program parameters, in particular user parameters, which are used to influence a low-temperature treatment, define, in particular, the temperature of the freezer-space space, in which the at least one sample is frozen and/or the information read process, which is preferably carried out when an article provided with an information medium is transferred from a user into the laboratory freezer.

A bioreactor comprises a container, in which specific microorganisms, cells, algae, plants, e.g. mosses, are cultivated (also: fermented) under conditions which are as ideal as possible. The operation of a bioreactor therefore is an application of biotechnology, which, in technical apparatuses, uses biological processes, in particular bioconversion or biocatalysis, or makes these available. Factors which can be controlled or monitored in most bioreactors, in particular by setting appropriate parameters, are the composition of the nutrient solution, the oxygen supply, temperature, pH, sterility and/or other factors. The purpose of cultivation in a bioreactor may be the harvesting of cells or constituents of cells, or the harvesting of metabolic products. By way of example, these can be used as an active ingredient in the pharmaceutical industry or as a basic chemical in the chemical industry. The breakdown of chemical compounds may also take place in bioreactors, such as e.g. in sewage water treatment in sewage works. The production of beer, wine and other such products likewise occurs in bioreactors. The most diverse type of organisms are cultivated in bioreactors for various purposes. A bioreactor can therefore have different configurations. It can be configured as stirred tank reactor, which can have a volume from a few milliliters to hundreds of liters and can be filled with nutrient solution. It can also be used or embodied as a fixed bed reactor or photobioreactor. A bioreactor can be part of a bioreactor system, preferably of a parallel bioreactor system. In such a parallel bioreactor system, a multiplicity of bioreactors are operated in parallel and controlled with high precision. A bioreactor, in particular the treatment apparatus thereof, comprises, in particular, a stirring apparatus for stirring the sample contained in the reactor container, in particular for stirring the nutrient solution. A bioreactor, in particular the treatment apparatus thereof, comprises, in particular, a pump apparatus for pumping the laboratory sample, which is preferably configured as nutrient solution. A bioreactor, in particular the treatment apparatus thereof, comprises, in particular, a setting apparatus for setting a gas content in the reactor container, in particular the content of $CO_2$ and/or $O_2$ or of dissolved oxygen (DO). A bioreactor, in particular the treatment apparatus thereof, comprises, in particular, a setting apparatus for setting, in particular regulating, a pH value in the sample in the reactor container. The instrument-controlled treatment of the at least one laboratory sample corresponds to, in particular, a nutrient solution treatment in a bioreactor, with at least one sample, preferably embodied as nutrient solution, being subjected to said treatment. Possible parameters, in particular program parameters, in particular user parameters, which are used to influence a nutrient solution treatment, define, in particular, the temperature of the nutrient solution in the reactor container and/or the speed of the stirrer apparatus, in particular the rotational speed and/or the pump speed or the metering speed and/or a gas content in the nutrient solution, in particular $CO_2$ and/or $O_2$ or dissolved oxygen (DO) and/or the pH value of the nutrient solution and/or at least one progress parameter, which influences or defines the progress, in particular the sequence, of a nutrient solution treatment program consisting of a plurality of steps.

A biological safety cabinet serves, in particular, for secure storage or stockpiling of hazardous materials, in particular for meeting a biological protection level. In particular, these levels are standardized in EU Directive 2000/54/EG on the protection of workers from risks related to exposure to biological agents at work and, in Germany, in the German Ordinance on Biological Substances. A biological safety cabinet is intended to prevent laboratory samples stored in a biological safety cupboard from endangering the surroundings if danger develops. In particular, safety is ensured by virtue of the atmosphere contained in the receiving region of the biological safety cabinet being replaced and, in particular, filtered. Here, in particular, this atmosphere is conveyed through the receiving region by a conveying apparatus and moved through a filter, which filters the atmosphere and, in particular, removes hazardous materials. The biological safety cabinet, in particular the treatment apparatus thereof, comprises, in particular, a conveying apparatus for conveying atmospheric gas, comprises, in particular, a timer apparatus for measuring a filter operation duration and a ventilator operation duration and/or comprises, in particular, a measurement apparatus for measuring a conveyed amount of atmospheric gas. The instrument-controlled treatment of the at least one laboratory sample corresponds, in particular, to an atmospheric gas treatment for treating the atmospheric gas, in which the at least one sample is stored, in a biological safety cabinet. Possible parameters, in particular program parameters, in particular user parameters, which are used to influence an atmospheric gas treatment, define, in particular, the temperature of the atmospheric gas in the receiving region and/or the flow speed of the atmospheric gas conveyed by the conveying apparatus, the amount of air conveyed, the filter operation duration and/or the ventilator operation duration.

A sample plate reader, also referred to as "plate reader" or "microplate reader", is a laboratory instrument for detecting biological, chemical or physical events of samples in microtitre plates. They are used widely in research: for active ingredient research, bioassay validation, quality control and manufacturing processes in the pharmaceutical and biotech industry and in academic organizations. The sample plate reader can, in particular, comprise at least one light source or radiation source, can comprise at least one photodetector, can comprise a temperature control apparatus for the temperature control of the samples or the sample plates and can comprise a timer. Sample reactions can be tested in 6-1536 well microtiter plates. The most common format for sample plates, in particular microtitre plates, which are used in academic research laboratories or in clinical-diagnostic laboratories, is a 96 well plate (an 8 by 12 matrix) with a typical individual volume of between 100 and 200 µl per well. microtiter plates with a higher density (384 or 1536 well microtiter plates) are typically used in screening applications if the throughput (number of samples to be processed per day) and assay costs per sample become critical parameters, and these have a typical assay volume of between 5 and 50 µl per well. The treatment is, in particular, an optical measurement of the microtiter plate, in particular the measurement of an absorption, fluorescence intensity, luminescence, time-resolved fluorescence and/or fluorescence polarization. Possible parameters, in particular program parameters, in particular user parameters, which are used to influence a measurement, define, for example, the intensity of the light source, the sensitivity of the photodetector, a time duration and/or a temperature.

A laboratory machine for treating fluid samples, in particular an automatic pipette, serves for the program-controlled treatment of these samples. A laboratory machine can be a laboratory instrument or comprise at least one laboratory instrument of the aforementioned type and/or can be embodied to carry out at least one, some or all of the treatments that can be executed by this aforementioned laboratory instrument. A laboratory machine comprises the treatment apparatus for automatic, program-controlled treatment of the at least one laboratory sample, wherein the treatment is controlled by using a plurality of program parameters, which are at least partly selected by the user. In the process, the sample can, for example, be moved and/or transported by the laboratory machine or a treatment apparatus of the laboratory machine. The movement can be brought about by transport in movable sample containers or by guidance through tube systems, capillaries or pipette tips. Here, liquid samples are, in particular, transported by suction, i.e. by pipetting, or, more generally, by the application of pressure differences. By way of example, a sample can be divided or diluted by a treatment of the sample. The contents of a sample can be analysed or it is possible, e.g. by way of a chemical reaction, for new contents to be produced, in particular by using the sample. In the context of, in particular, handling and analysing DNA or RNA or the constituents thereof, laboratory machines aid in obtaining a wealth of information within a suitable period of time or in analysing many such samples. This treatment apparatus of a laboratory machine usually comprises a worktop with workstations, on which samples can be handled or stored in various ways. For the purposes of transporting e.g. liquid samples between various positions, in particular sample containers, the treatment apparatus usually comprises an instrument-controlled movement device and an instrument-controlled fluid-transfer apparatus, which can e.g. comprise a pipetting system. Both the transport of the samples and the treatment thereof at the various stations can be carried out in an instrument-controlled manner, in particular in a program-controlled manner. Then the treatment is preferably at least partly or completely automated.

The user of the laboratory machine can preferably set the type of treatment for the sample. Such a treatment type may, in particular, serve for:

nucleic acid purification, in particular:
"MagSep Blood gDNA": purification of genomic DNA from whole blood, in particular using the Eppendorf® MagSep Blood gDNA kit;
"MagSep Tissue gDNA": purification of genomic DNA from living tissue, in particular using the Eppendorf® MagSep Tissue gDNA kit;
"MagSep Viral DANN/RNA": purification of viral RNA or DNA from cell-free bodily fluids, in particular using the Eppendorf® MagSep Viral DNA/RNA kit;

and PCR applications, in particular:
"Compose Mastermix";
"Normalize Concentrations";
"Create Dilution Series";
"Setup Reactions".

A laboratory instrument, in particular the laboratory machine, is preferably embodied in such a way that the treatment of the at least one laboratory sample can be controlled automatically using the acquired program parameters. The laboratory instrument, in particular the laboratory machine, in particular the control program thereof, is preferably embodied in such a way that the input undertaken by the user, in particular the at least one value of at least one program parameter, can be used, where necessary, to automatically establish further, required program parameters, in particular by calculation or comparison with data in a database of the laboratory machine. In particular, the control parameters preferably used for performing the treatment in detail are preferably determined automatically. As a result of these measures, the operation of the laboratory machine convenient, the user is spared from, in particular, designing a program code since these steps are carried out, in particular automatically, by the laboratory instrument, in particular the laboratory machine. In a preferred embodiment, all that is required from the user are the entries which are directly related to the treatment of the samples to be performed. Often, these are the same specifications that would also be necessary for performing the treatment manually and these are known to the user. By contrast, the parameters which relate to the control of the laboratory instrument, in particular of the laboratory machine, in particular the control parameters, need not be set in detail since these are preferably set automatically. Control parameters are the parameters required in detail for controlling the technical constituents of the treatment apparatus. Control parameters can be program parameters or can be parameters derived therefrom for the technical implementation, in particular automatically determined parameters.

Preferably, a laboratory instrument, in particular the laboratory machine, automatically selects the fitting set of program parameters following the treatment type selection by the user, wherein the program parameters thereof required on part of the user are then queried from the user in steps (b) and (c). The set of program parameters can contain, firstly, the program parameters required on part of the user and can contain, secondly, further program parameters. These further program parameters can be set automatically depending on the selected treatment of type or can be set automatically depending on at least one or all program parameters entered by the user and/or can be stored in the storage apparatus. The stored parameter sets are preferably optimized for the type of treatment—or become optimized by the laboratory instrument, in particular the laboratory machine—such as that the user preferably requires no specialist knowledge for optimizing the parameters. The control parameters which are necessary for performing the specific treatment by means of the treatment apparatus are derived from the program parameter set.

A program parameter set of program parameters specific to a treatment type is preferably defined for this treatment type. The program parameters of this program parameters set can, in particular, define the accessories to be used for the treatment, e.g. sample container, transport container and/or the further consumables and/or tools to be used.

The mapping between program parameter set and treatment type is stored in the storage apparatus of the laboratory instrument, in particular of the laboratory machine. Preferably, a laboratory instrument, in particular the laboratory machine, is embodied in such a way that the user can store and/or use more such mappings in a laboratory instrument, in particular the laboratory instrument. The operation of the laboratory instrument becomes particularly efficient by these mappings in combination with the clear and well-structured querying of the program parameters. This mapping is preferably brought about by using one or more program modules, wherein a program module is respectively tailored to a specific application:

Preferably, the laboratory instrument, in particular the laboratory machine, comprises at least one program module, with a predetermined program module serving for controlling a predetermined laboratory problem for treating laboratory samples.

A laboratory instrument according to the invention is preferably capable to work independently, i.e. as a stand-alone instrument, which means it may require some user input but does not require a data connection with a further device, e.g. a central control computer, in order to work in a conventional operating mode. The conventional operating mode of the laboratory instrument provides the treatment of the at least one laboratory sample using its treatment apparatus.

The invention furthermore relates to a method for configuring a laboratory instrument, wherein the laboratory instrument serves for the instrument-controlled treatment of at least one laboratory sample, by means of a configuration control device, in particular by means of a configuration control device according to the invention, wherein the configuration control device comprises a control apparatus with an access control device, by means of which an identification of users can be performed, and wherein data can be processed in the control apparatus, which data contain user-dependent configuration data for configuring the laboratory instrument, in particular for configuring a control program or process program used on the laboratory instrument, wherein the method comprises the following steps:

identifying a user by means of the access control device of the control apparatus; and
configuring the laboratory instrument or configuring a treatment using user-dependent configuration data.

Preferred configurations of the method according to the invention can be derived from the description of the configuration control device according to the invention and of the laboratory instrument according to the invention and from the preferred configurations thereof.

Further preferred configurations of the configuration control device according to the invention and of the laboratory instrument according to the invention and of the method according to the invention emerge from the following description of the exemplary embodiments in conjunction with the figures and the description thereof. If nothing else is described or if nothing else emerges from the context, the same components of the exemplary embodiments are substantially characterized by the same reference signs. In detail:

FIG. 1 schematically shows an exemplary embodiment of the configuration control device according to the invention.

Figure 1:
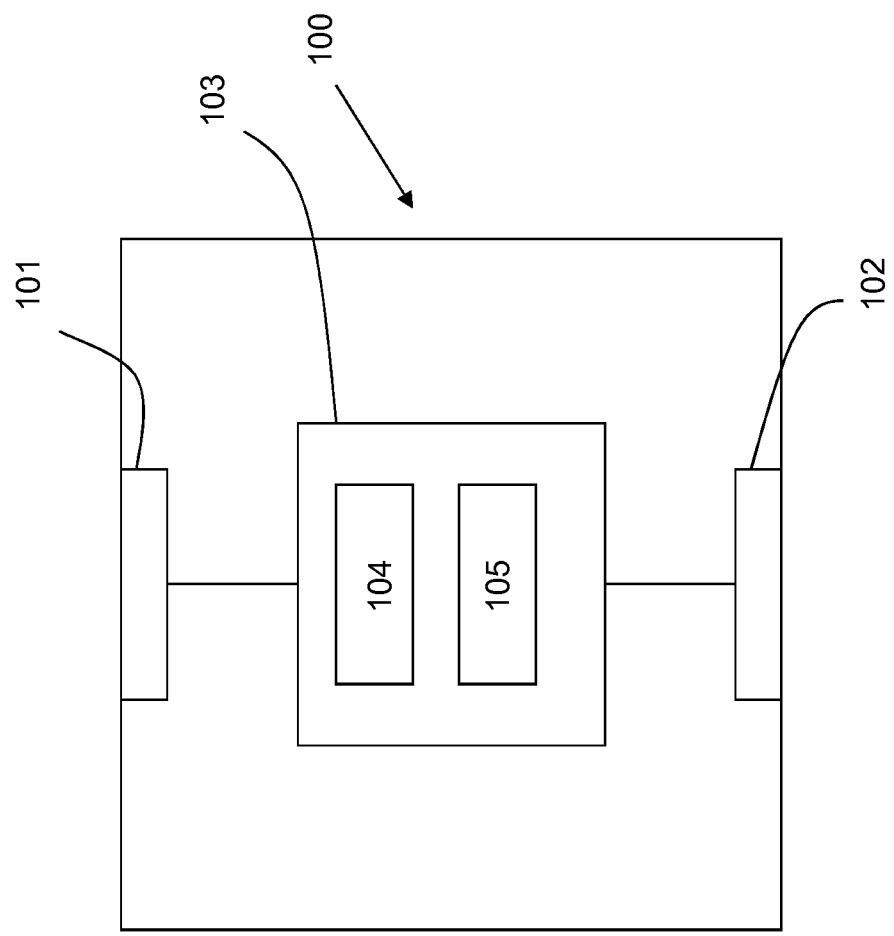

FIG. 1 shows the configuration control device 100. The configuration control device 100 is configured for a laboratory instrument, which serves for the instrument-controlled treatment of a laboratory sample, in particular for the laboratory instrument 1 in FIG. 2, wherein the configuration control device 100 comprises: an interface apparatus 101 for establishing a first data connection to a user interface apparatus and an interface apparatus 102 for establishing a second data connection to a control apparatus of the laboratory instrument; and a control apparatus 103. It has an access control device 104 for identifying a user accessing via the first data connection and a data processing apparatus 105 for processing predetermined user-dependent configuration data. The control apparatus 103 is configured to identify an accessing user and to transfer the user-dependent configuration data assigned to the identified user to the laboratory instrument 1 via the second data connection, in order, thereby, to configure said laboratory instrument in a user-dependent manner.

Figure 2:
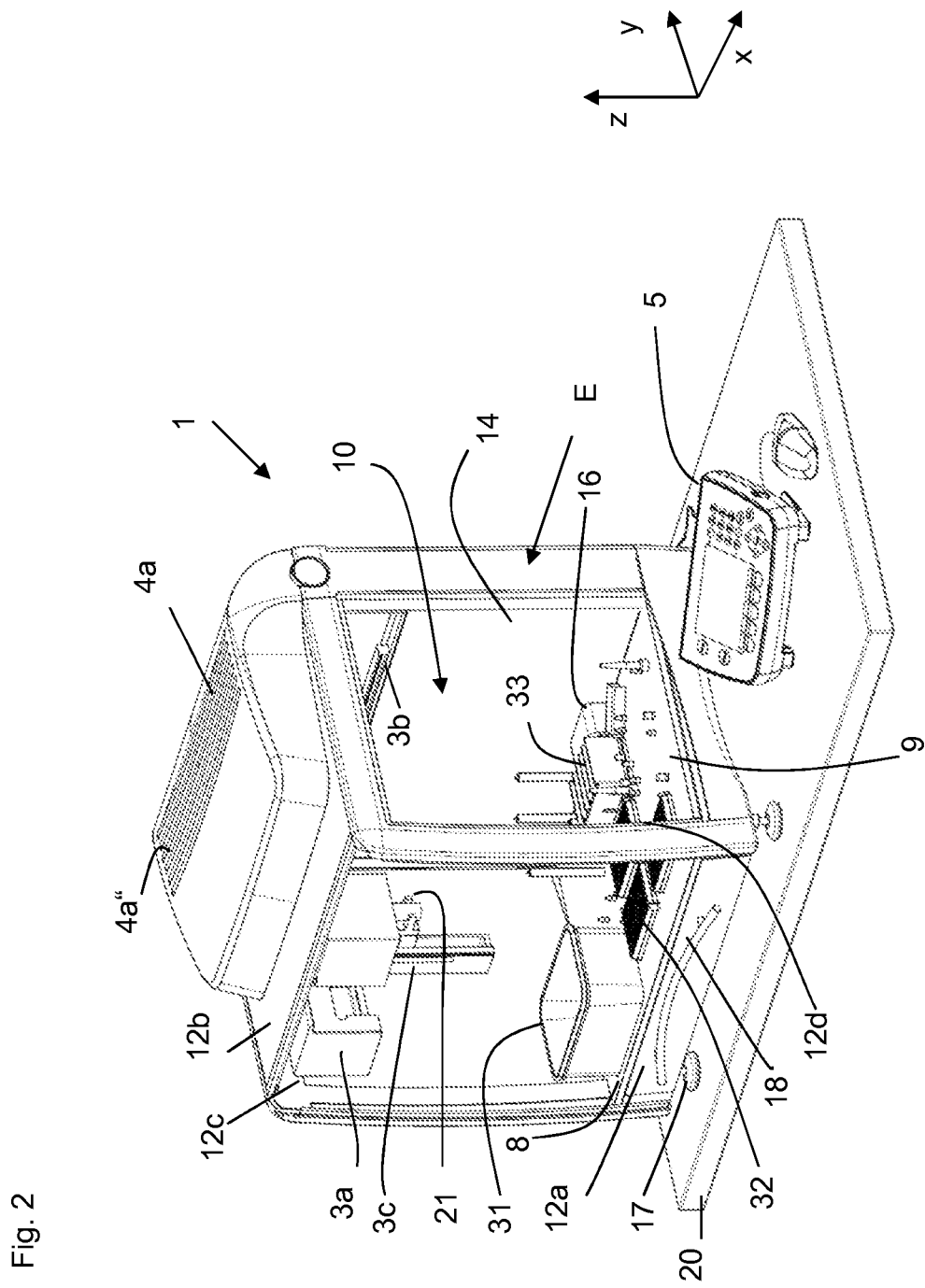
FIG. 2 shows an exemplary embodiment of the laboratory instrument according to the invention, which comprises a configuration control device according to the invention.

FIG. 2 shows the laboratory instrument 1, which is embodied here as a laboratory machine 1 for treating fluid samples, to be precise as a pipetting machine (laboratory machine). The laboratory machine 1 serves for the program-controlled treatment of these samples.

FIG. 2 shows the laboratory machine 1 for automated processing of liquid samples, in particular for the program-controlled treatment of liquid samples. The laboratory machine 1 is a table-top instrument and disposed on the work table 20 with the four feet 17 thereof. It comprises an electronic control apparatus 2 (not shown here), which is suitable for processing program code for the program-controlled treatment of the liquid samples. The control apparatus 2 is attached in the control space, which is denoted by the arrow E and separated from the workspace 10 by a vertical wall 14. The control space also harbours the voltage supply components which supply the suitable supply voltage for the electrical components of the laboratory machine. The control apparatus 103 of the configuration control device 100 from FIG. 1 is integrated into the control apparatus 2.

The laboratory machine 1 comprises a treatment space 10 for receiving the liquid samples to be treated, a sample handling apparatus 3, controllable in a program-controlled manner, for performing at least one program-controlled treatment step on the at least one sample, which is disposed in the handling space. The components 3a, 3b, 3c and 3d of the movement apparatus are assigned to the sample handling apparatus 3.

The laboratory machine 1 comprises a housing 12 comprising a front side 12a, a rear side 12f (not shown here) disposed opposite to the front side, a top side 12b, a bottom side 12e (not shown here) disposed opposite to the top side and two lateral sides 12c and 12d lying opposite one another. The sides 12a, 12b and 12c are substantially made of a material transparent to visible light.

The front side 12a, which is substantially embodied like door 12a, namely a sliding door 12a, can be moved by hand and/or moved in a program-controlled manner and can close downward, substantially along the z-axis of the Cartesian coordinate system. FIG. 2a shows the closed position of the door 12a.

The treatment space 10 is delimited by the front side 12a and the two side faces 12c and 12d, as well as the wall 14 and the worktop 8, which forms the upper side of the base plate 9. The worktop 8 provides six handling stations. The handling stations are substantially planar areas in the handling region 8. Pins serve to align the lab-ware, that is to say e.g. the thermorack 33, microtiter plates 32 and waste container 31, at the respective handling station. The exact positioning enables precise, robot-controlled addressing of the sample containers, in particular of the depressions in the microtitre plates 32. A magnetic separation device 16 is disposed in the vicinity of the wall 14, where a thermorack 33, i.e. a temperature-controlled sample vessel holder, is disposed. The magnetic fork (not shown here) of the magnetic separation device 16 enters corresponding receiving channels of the thermorack from the side in order to develop the magnetic effect thereof laterally on the laboratory vessels (sample tubules).

The laboratory machine 1 comprises two decontamination apparatuses, an electronically controllable air purification device 4a, 4a" for purifying the air in the treatment space, which is controlled electronically and digitally by the control apparatus and which comprises a ventilating device. The ventilation device comprises three ventilators (not depicted here), which transport an air flow from outside of the device into the treatment space.

The control apparatus 2 comprises a control program. The laboratory machine 1 comprises a sample handling apparatus 3, which comprises a movement apparatus with three guide-rail elements 3a, 3b, 3c, which correspond to movements along the y, x and z-axis of the Cartesian coordinate system. Electronically regulable linear motors are provided for driving the movement along the desired direction. In this manner, the assembly head 21 can be moved into each desired position accessible in the handling space 10. The movement apparatus is part of a robotic system of the sample handling apparatus 3. The assembly head 21 can be transported thereby in a program-controlled manner. A tool instrument, e.g. a pipetting head or a gripper, is connectable to the assembly head. The components disposed in the treatment space, in particular the sample handling apparatus 3, are components of the treatment device of the laboratory machine.

Figure 3:
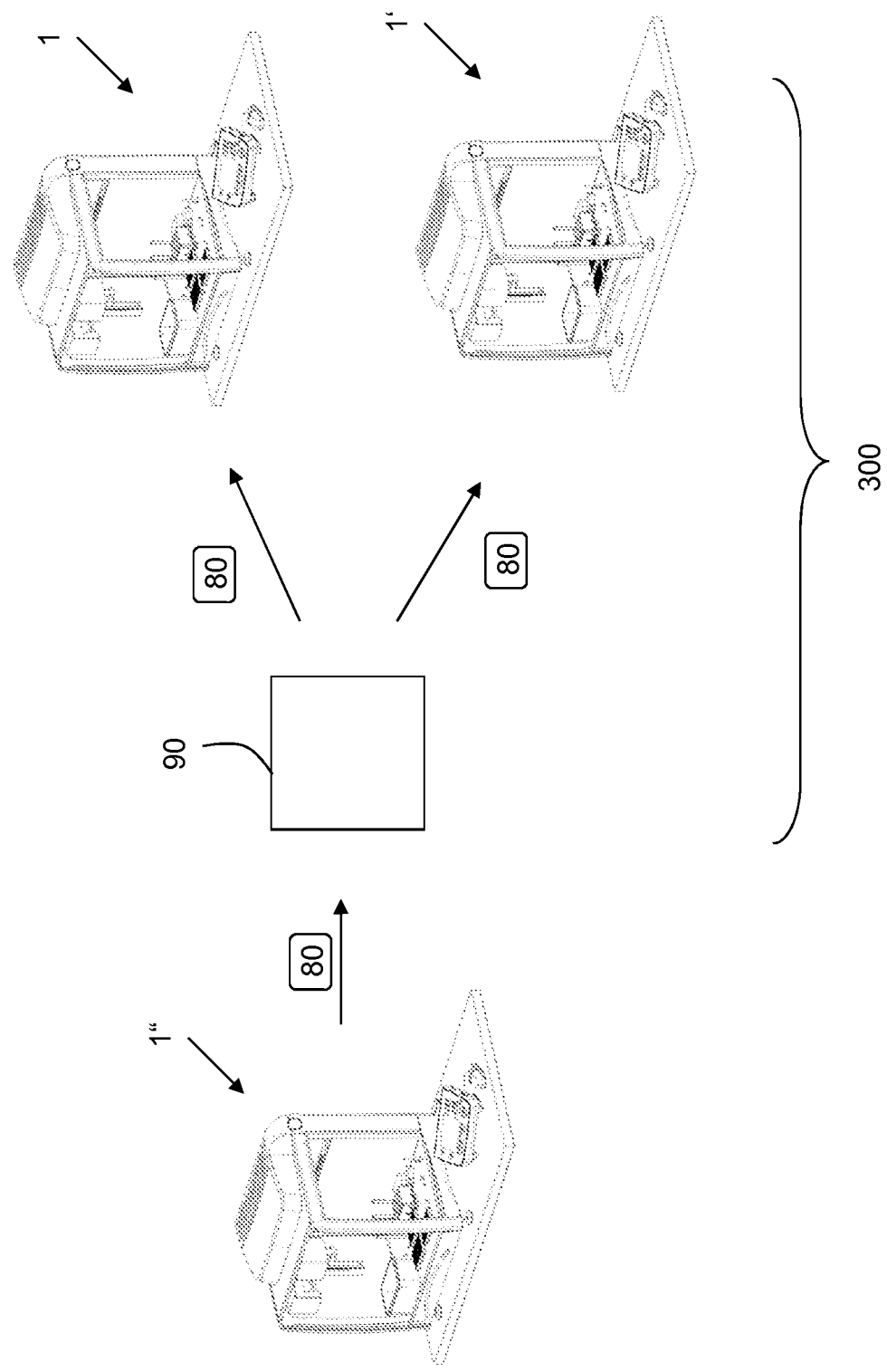
FIG. 3 shows an exemplary embodiment of the system 300 according to the invention, which comprises a server and at least one laboratory instrument 1.

The laboratory machine comprises a user interface apparatus 5 configured as a module, by means of which the user can log onto the laboratory machine locally. He is then identified by the access control device of the configuration control device. In the present example, the configuration control device transmits the identification data of the user to an external server 90 (see FIG. 3) and receives the user-dependent configuration data 80 from the external server 90. The laboratory instrument 1 is configured automatically on the basis of the configuration data 80. The user-dependent configuration data 80 can e.g. have been set previously by the user on a laboratory instrument 1' (FIG. 3). In accordance with one aspect of the invention, the user can use any laboratory instrument 1, 1' (FIG. 3) which can use these user-dependent configuration data 80 for configuration purposes, without once again setting the configuration data or at least a part thereof on said respective laboratory instrument. In particular, the accustomed user-dependent user interface is indicated to the user on the indication apparatus of the user interface 5 on the laboratory instruments 1, 1' configured as a function of the user.

Figure 4:
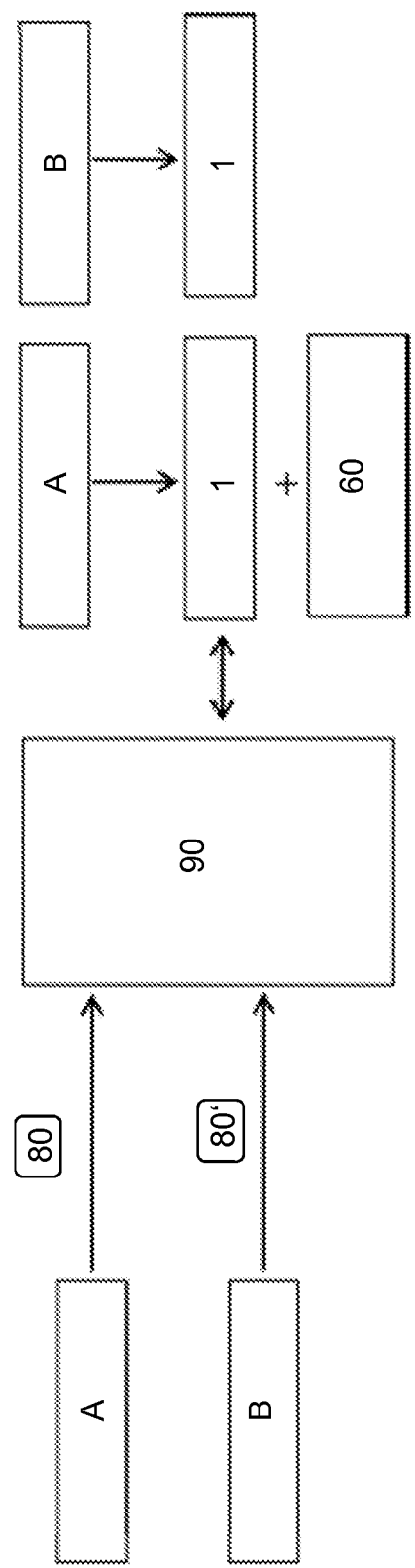
FIG. 4 shows how an exemplary embodiment of the method according to the invention with a configuration control device according to the invention can be used.
Figure 5:
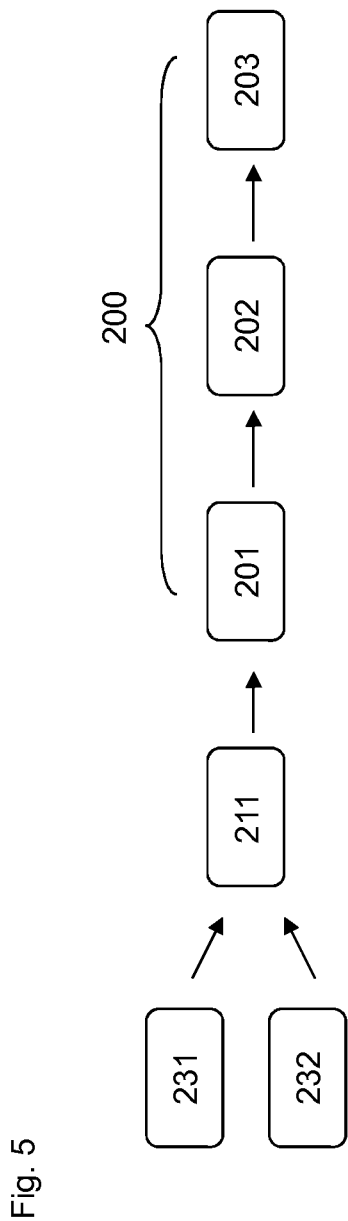
FIG. 5 shows an exemplary embodiment of the method according to the invention for configuring a laboratory instrument.

FIG. 4 shows how an exemplary embodiment of the method according to the invention with a configuration control device according to the invention can be used. In this example, the case is compared where user A initially uses the laboratory instrument 1 and user B subsequently uses the same laboratory instrument 1. User A is an inexperienced user and user B is an experienced user. Initially, user-dependent configuration data 80, which can be assigned to user A, and user-dependent configuration data 80', which can be assigned to user B, must exist. The user-dependent configuration data can be assigned manually to the respective user or they can be assigned automatically on the basis of a criterion. The latter is the case here. On the basis of the qualification of the user, which was set in advance and which is uniquely linked to his identification data, the user-dependent configuration data assigned to the qualification are assigned to each user (steps 231, 232 in FIG. 5). The information about these assignments is stored in a database of the server 90. The user-dependent configuration data are stored and kept available on the server 90. If user A now logs onto the laboratory instrument 1 (step 211 in FIG. 5), the user is identified by the access control device of the configuration control device (step 201 in FIG. 5), in particular by means of an authentication method. The laboratory instrument transmits the identification data to the server 90 and receives from the latter the corresponding user-dependent configuration data 80 (step 202 in FIG. 5). Depending on these configuration data, the configuration control device configures the laboratory instrument in a user-dependent manner (step 203 in FIG. 5), namely differently for the inexperienced user A than for the experienced user B. The inexperienced user A obtains a configuration which provides for a help file 60 to be made available to user A via the user interface of the user interface apparatus 5. This is not provided in the case of user B. In this manner, use of the laboratory instrument 1 becomes easier for user A and the productivity in the laboratory is improved.

Figure 6:
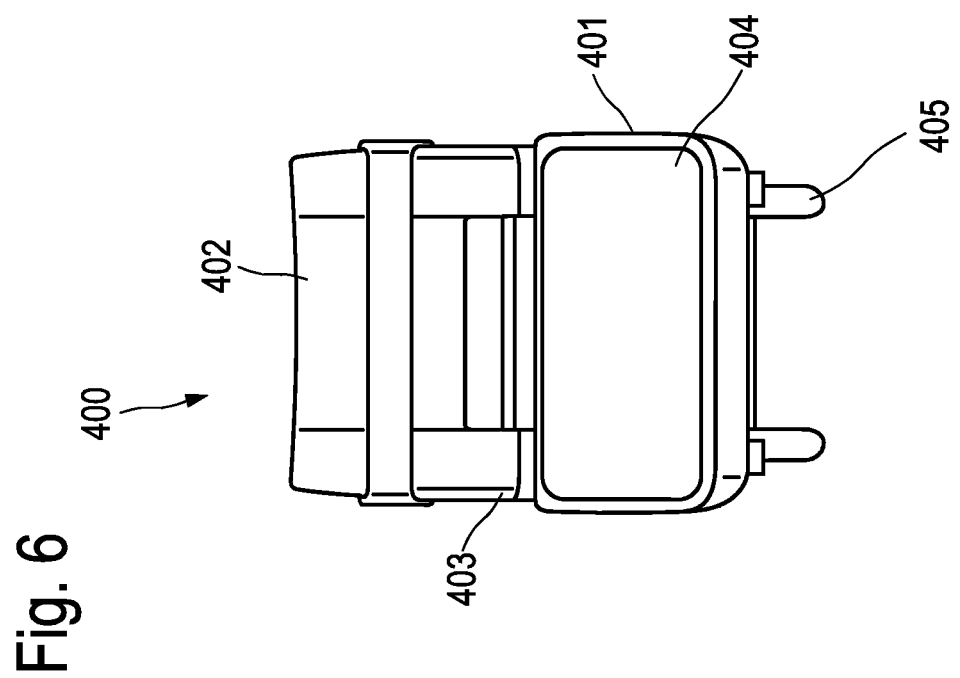
FIG. 6 shows a further exemplary embodiment of the laboratory instrument according to the invention, in this case a thermocycler.

FIG. 6 shows, as a further exemplary embodiment, the laboratory instrument 400, a thermocycler. The laboratory instrument 400 is a tabletop instrument and disposed with its feet 405 on a worktable (not depicted here). It comprises an electronic control apparatus 406 (not shown here), which is suitable for processing program code for the program-controlled treatment of the generally liquid samples. The treatment is usually a time-controlled temperature control. The control apparatus 406 comprises an access control device for identifying a user accessing via the first data connection and a data processing apparatus for processing predetermined user-dependent configuration data, wherein these configuration data can be used for the user-dependent treatment of the at least one laboratory sample, wherein the control apparatus is configured to identify an accessing user and to transfer the user-dependent configuration data assigned to the identified user to the laboratory instrument via a second data connection, in order, thereby, to configure said laboratory instrument in a user dependent manner.

The control apparatus 406 is housed in the housing 401. The housing also harbours the voltage supply components which supply the suitable supply voltage for the electrical components of the laboratory instrument. The control apparatus of the access control device is integrated into the control apparatus 406.

The laboratory instrument 400 comprises a treatment space 403 for holding the liquid samples to be treated. The treatment space comprises at least one treatment apparatus 407 (not depicted here) for carrying out at least one program-controlled treatment step on the at least one sample which is disposed in the treatment space.

The control apparatus 406 comprises a control program.

The laboratory instrument comprises a user interface apparatus 404, by means of which a user can log onto the laboratory instrument locally.

Figure 7:
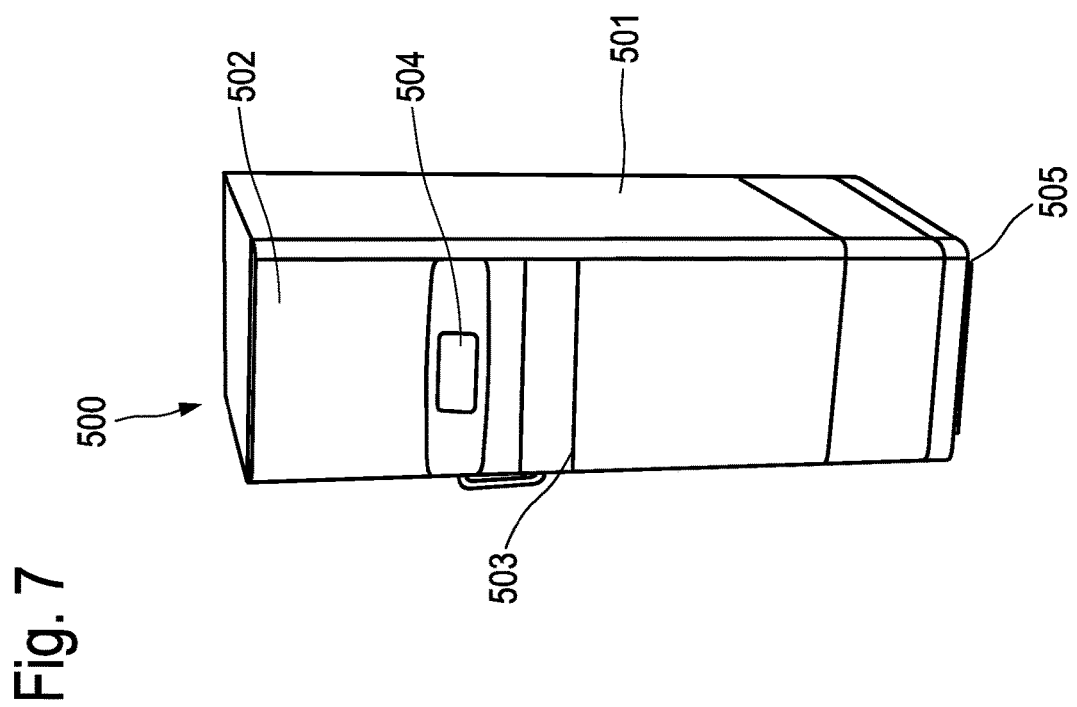
FIG. 7 shows, as a further exemplary embodiment of the laboratory instrument according to the invention, a laboratory freezer.

FIG. 7 shows, as a further exemplary embodiment, the laboratory instrument 500, a laboratory freezer. The laboratory instrument is a standing instrument which is positioned on the floor (not depicted here) with the feet 505. It comprises an electronic control apparatus 506 (not shown here), which is suitable for setting, regulating and monitoring the temperature control of the laboratory instrument by means of a program code and for controlling the treatment of the generally liquid samples. The treatment is usually temperature control. The control apparatus 506 comprises an access control device for identifying a user accessing via the first data connection and a data processing apparatus for processing predetermined user-dependent configuration data, wherein these configuration data can be used for the user-dependent treatment of the at least one laboratory sample, wherein the control apparatus is configured to identify an accessing user and to transfer the user-dependent configuration data assigned to the identified user to the laboratory instrument via a second data connection, in order, thereby, to configure said laboratory instrument in a user dependent manner.

The control apparatus 506 is housed in the housing 501. The housing also harbours the voltage supply components which supply the suitable supply voltage for the electrical components of the laboratory instrument. The control apparatus of the access control device is integrated into the control apparatus 506.

The laboratory instrument 500 comprises a treatment space 503 for holding the liquid samples to be treated. The treatment space comprises at least one treatment apparatus 507 (not depicted here) for carrying out at least one program-controlled treatment step on the at least one sample which is disposed in the treatment space. The program-controlled treatment step in this case is the permanent temperature control at a defined temperature.

The control apparatus 506 comprises a control program.

The laboratory instrument comprises a user interface apparatus 504, by means of which a user can log onto the laboratory instrument locally.

APPENDIX 1

Possible program parameters as a function of the laboratory instrument type

| Instrument | Most important parameter | | | | Sequence programming |
|---|---|---|---|---|---|
| Centrifuge | Temperature | Speed | | Time | No, steps conceivable |
| Cycler | Temperature | | | Time | Steps |
| Biospectrometer | Temperature (kinetic) | | | Result | Complex process |
| Plate reader | Temperature | Sample number | | Result | Complex process |
| Cell counter | | | | Result | Complex process |
| Incubator | Temperature | CO2/O2 | Relative humidity | Time | No, steps conceivable |
| (Thermal) mixer | Temperature | Speed | | Time | Restricted steps |
| Shaker | Temperature | Speed | | | Steps |
| Pipetting control device | Sample volume | | Pipetting tools | Transfer type | Restricted steps |
| Freezer | Temperature | Alarm value | | | No |
| Laboratory machine | Sample number | Sample volume | Pipetting tools | Source/Target | Transfer type (pipetting/dispensing) | Complex process |
| Fermenter/bioreactor | Stirrer rotational speed | Dissolved oxygen (DO) | pH | Metering speed (pumps) | |
| Biosafety cabnient | Flow speed | Filter service life | Ventilator service life | Amount of air | |

| Use cases to be considered (examples): | Remote monitoring |
| | Remote control |
| | Booking schedule |
| | Service access |
| | Pre-programming |
| Roles to be considered (examples): | Admin |
| | LabUser |
| | Inexperienced |
| | Manager |
| | Service |
| Instruments to be considered (examples): | Cycler | n treatment apparatuses (thermoblocks) |
| | Centrifuge | 1 treatment apparatus (rotor) |
| Assumption: Access permissions are independent of the instrument | Shaker | 1 treatment apparatus (shaker platform, a plurality thereof also conceivable) |
| | Incubator | 1 treatment apparatus |
| | Cell counter | 1 treatment apparatus |
| | BSC | 1 treatment apparatus |
| | Freezer | n treatment apparatuses conceivable (differently actuatable cooling levels) |
| | Biospectrometer | 1 treatment apparatus |

Use Case: Remote Monitoring

| | User: Admin | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |

-continued

| User: Admin ||| 
|---|---|---|
| State | Role logged in | Access possible? |
| Booking = idle? | Admin | Y |
|  | LabUser | Y |
|  | Inexperienced | Y |
|  | Manager | Y |
| Standby | — | Y |

Use Case: Remote Monitoring

| User: LabUser ||| 
|---|---|---|
| State | Role logged in | Access possible? |
| Idle (ready) | Admin | Y |
|  | LabUser | Y |
|  | Inexperienced | Y |
|  | Manager | Y |
| Programmed = idle? | Admin | Y |
|  | LabUser | Y |
|  | Inexperienced | Y |
|  | Manager | Y |
| Started (running) | Admin | Y |
|  | LabUser | Y |
|  | Inexperienced | Y |
|  | Manager | Y |
| Stopped (finished) = idle? | Admin | Y |
|  | LabUser | Y |
|  | Inexperienced | Y |
|  | Manager | Y |
| Standby | — | Y |

Use Case: Remote Monitoring

| State | Role logged in | Access possible? |
|---|---|---|
| User: Inexperienced |||
| Idle (ready) | Admin | N |
|  | LabUser | N |
|  | Inexperienced | N |
|  | Manager | N |
| Programmed = idle? | Admin | N |
|  | LabUser | N |
|  | Inexperienced | N |
|  | Manager | N |
| Started (running) | Admin | N |
|  | LabUser | N |
|  | Inexperienced | N |
|  | Manager | N |
| Stopped (finished) = idle? | Admin | N |
|  | LabUser | N |
|  | Inexperienced | N |
|  | Manager | N |
| Standby | — | Y |
| User: Manager |||
| Idle (ready) | Admin | Y |
|  | LabUser | Y |
|  | Inexperienced | Y |
|  | Manager | Y |
| Programmed = idle? | Admin | Y |
|  | LabUser | Y |
|  | Inexperienced | Y |
|  | Manager | Y |
| Started (running) | Admin | Y |
|  | LabUser | Y |
|  | Inexperienced | Y |
|  | Manager | Y |

-continued

| State | Role logged in | Access possible? |
|---|---|---|
| Stopped (finished) = idle? | Admin | Y |
|  | LabUser | Y |
|  | Inexperienced | Y |
|  | Manager | Y |
| Standby | — | Y |

Use Case: Remote Control

| User: Admin |||
|---|---|---|
| State | Role logged in | Access possible? |
| Idle (ready) | Admin | N |
|  | LabUser | Y |
|  | Inexperienced | Y |
|  | Manager | Y |
| Programmed = idle? | Admin | N |
|  | LabUser | Y |
|  | Inexperienced | Y |
|  | Manager | Y |
| Started (running) | Admin | N |
|  | LabUser | Y |
|  | Inexperienced | Y |
|  | Manager | Y |
| Stopped (finished) = idle? | Admin | N |
|  | LabUser | Y |
|  | Inexperienced | Y |
|  | Manager | Y |
| Booking = idle? | Admin | N |
|  | LabUser | Y |
|  | Inexperienced | Y |
|  | Manager | Y |
| Standby | — | N |

Use Case: Remote Control

| User: LabUser |||
|---|---|---|
| State | Role logged in | Access possible? |
| Idle (ready) | Admin | N |
|  | LabUser | N |
|  | Inexperienced | Y |
|  | Manager | N |
| Programmed = idle? | Admin | N |
|  | LabUser | N |
|  | Inexperienced | Y |
|  | Manager | N |
| Started (running) | Admin | N |
|  | LabUser | N |
|  | Inexperienced | Y |
|  | Manager | N |
| Stopped (finished) = idle? | Admin | N |
|  | LabUser | N |
|  | Inexperienced | Y |
|  | Manager | N |
| Booking = idle? | Admin | N |
|  | LabUser | N |
|  | Inexperienced | Y |
|  | Manager | N |
| Standby | — | N |

Use Case: Remote Control

| | User: Inexperinced | |
|---|---|---|
| State | Role logged in | Access possible? |
| Idle (ready) | Admin | N |
| | LabUser | N |
| | Inexperienced | N |
| | Manager | N |
| Programmed = idle? | Admin | N |
| | LabUser | N |
| | Inexperienced | N |
| | Manager | N |
| Started (running) | Admin | N |
| | LabUser | N |
| | Inexperienced | N |
| | Manager | N |
| Stopped (finished) = idle? | Admin | N |
| | LabUser | N |
| | Inexperienced | N |
| | Manager | N |
| Booking = idle? | Admin | N |
| | LabUser | N |
| | Inexperienced | N |
| | Manager | N |
| Standby | — | N |

Use Case: Remote Control

| | User: Manager | |
|---|---|---|
| State | Role logged in | Access possible? |
| Idle (ready) | Admin | N |
| | LabUser | Y |
| | Inexperienced | N |
| | Manager | N |
| Programmed = idle? | Admin | N |
| | LabUser | Y |
| | Inexperienced | N |
| | Manager | N |
| Started (running) | Admin | N |
| | LabUser | Y |
| | Inexperienced | N |
| | Manager | N |
| Stopped (finished) = idle? | Admin | N |
| | LabUser | Y |
| | Inexperienced | N |
| | Manager | N |
| Booking = idle? | Admin | N |
| | LabUser | Y |
| | Inexperienced | N |
| | Manager | N |
| Standby | — | N |

Use Case: Booking Schedule

| | User: Admin | |
|---|---|---|
| State | Role logged in | Access possible? |
| Idle (ready) | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |

-continued

| | User: Admin | |
|---|---|---|
| State | Role logged in | Access possible? |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use Case: Booking Schedule

| | User: LabUser | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use Case: Booking Schedule

| | User: Inexperienced | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use Case: Booking Schedule

| | User: Manager | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use Case: Pre-Programming

| | User: Admin | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use Case: Pre-Programming

| | User: LabUser | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use Case: Pre-Programming

| | User: Inexperienced | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use Case: Pre-Programming

| | User: Manager | |
|---|---|---|
| State | Role logged in | Access possible? |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use Case: Remote Service Access

| State | Role logged in | Access possible? |
|---|---|---|
| Idle (ready) | Admin | Y |
|  | LabUser | N |
|  | Inexperienced | N |
|  | Manager | Y |
| Programmed = idle? | Admin | Y |
|  | LabUser | N |
|  | Inexperienced | N |
|  | Manager | Y |
| Started (running) | Admin | Y |
|  | LabUser | N |
|  | Inexperienced | N |
|  | Manager | Y |
| Stopped (finished) = idle? | Admin | Y |
|  | LabUser | N |
|  | Inexperienced | N |
|  | Manager | Y |
| Booking = idle? | Admin | Y |
|  | LabUser | N |
|  | Inexperienced | N |
|  | Manager | Y |
| Standby | — | Y |

User: Service

The invention claimed is:

1. A laboratory instrument (1; 1'; 1") for the instrument-controlled treatment of at least one laboratory sample, said laboratory instrument comprising:
the laboratory instrument being selected from the group of laboratory instruments including at least a laboratory centrifuge, a thermocycler, a laboratory spectrophotometer, an optical cell counting instrument, a laboratory incubator, a laboratory shaker, a laboratory mixer, a laboratory freezer, a bioreactor, a biological safety cabinet, a sample plate reader, and a laboratory machine for treating fluid samples,
a) a configuration control device (100) for the user-dependent configuration of said laboratory instrument for the instrument-controlled treatment of at least one laboratory sample, said configuration control device (100) comprising:
  i) at least one interface apparatus for establishing a first data connection to a user interface apparatus and for establishing a second data connection to a control apparatus of a laboratory instrument;
  ii) a control apparatus, comprising an access control device for identifying a user accessing via the first data connection and
  iii) a data processing apparatus for processing predetermined user-dependent configuration data, wherein this configuration data can be used for the user-dependent treatment of the at least one laboratory sample,
  wherein the control apparatus of the configuration control device (100) is configured:
    to identify an accessing user and
    to forward user-dependent configuration data, assigned to the identified user, to the laboratory instrument via a second data connection in order, thereby, to configure said laboratory instrument in a user-dependent manner;
b) at least one treatment apparatus for instrument-controlled treatment of the at least one laboratory sample;
c) a control apparatus for the user-dependent control of the at least one treatment apparatus;
wherein the control apparatus of the laboratory instrument is configured:
to receive user-dependent configuration data from the configuration control device and
to control the laboratory instrument in accordance with the user-dependent configuration data,
wherein the at least one interface apparatus of the configuration control device (100) is embodied to establish at least one third data connection to at least one external data processing apparatus, which comprises a storage apparatus on which configuration data can be stored,
and wherein the control apparatus of the configuration control device is embodied to receive configuration data via the at least one third data connection;
wherein the control apparatus of the configuration control device (100) is embodied:
to evaluate the configuration data received via the at least one third data connection and to assign user-dependent configuration data to the identified user; and
wherein the laboratory instrument is configured to use the user-dependent configuration data for the user-dependent treatment of the at least one laboratory sample,
wherein the control apparatus of the laboratory instrument is embodied, as a function of the identified user, to use the user-dependent configuration data which determine a set of user-dependent program parameters, by means of which a program-controlled treatment is controlled by determining the movement and/or transport and/or examination and/or modification of the at least one laboratory sample in a user-dependent manner by means of the treatment apparatus,
the program parameters being determined by the user-dependent configuration data and determining the treatment being selected from the following group of program parameters including
a temperature of a laboratory centrifuge, a rotational speed of a laboratory centrifuge, a time parameter of a rotation or a temperature setting and/or at least one progress parameter of a laboratory centrifuge, which influences or defines the progress, in particular the sequence, of a rotation program consisting of a plurality of rotation steps,
a temperature of a temperature level of a thermocycler, the duration of a temperature level of a thermocycler, a number of temperature levels or cycles and/or at least one progress parameter of a thermocycler, which influences or defines the progress, in particular the sequence, of a temperature monitoring program consisting of a plurality of steps,
an optical light spectrum of a laboratory spectrophotometer, by means of which the at least one sample is irradiated and/or at least one progress parameter of a laboratory spectrophotometer, which influences or defines the progress, in particular the sequence, of a light and measurement treatment program consisting of a plurality of steps,
a light intensity of a light source of an optical cell counting instrument, by means of which the at least one sample is irradiated and/or at least one progress parameter of an optical cell counting instrument, which influences or defines the progress, in particular the sequence, of a light and measurement treatment program or a pumping and measurement treatment program consisting of a plurality of steps,
a temperature of an incubator space of a laboratory incubator, in which the at least one sample is incubated, the $O_2$ and/or $CO_2$ partial pressure in the incubator interior, a humidity in the incubator interior and/or at least one progress parameter of a laboratory incubator, which influences or defines the progress, in particular the sequence, of an incubation treatment program consisting of a plurality of steps, a movement intensity of a laboratory shaker, in particular a movement frequency in the case of an oscillating drive, a time period during a shaker treatment and/or at least one progress parameter of a laboratory shaker, which influences or defines the progress, in particular the sequence, of a shaker treatment program consisting of a plurality of steps, a movement intensity of a laboratory mixer, in particular the movement frequency in the case of an oscillating drive, a time period during a mixer treatment and/or at least one progress parameter of a laboratory mixer, which influences or defines the progress, in particular the sequence, of a mixer treatment program consisting of a plurality of steps, a temperature of a freezer-space of a laboratory freezer, in which the at least one sample is frozen and/or an information read by a read process, which is preferably carried out when an article provided with an information medium is transferred from a user into the laboratory freezer, a temperature of a nutrient solution in a reactor container and/or a speed of a stirrer apparatus of a bioreactor, in particular a rotational speed and/or a pump speed or a metering speed and/or a gas content in the nutrient solution, in particular $CO_2$ and/or $O_2$ or dissolved oxygen (DO) and/or the pH value of the nutrient solution and/or at least one progress parameter of a bioreactor, which influences or defines the progress, in particular the sequence, of a nutrient solution treatment program consisting of a plurality of steps, a temperature of an atmospheric gas in a receiving region and/or a flow speed of the atmospheric gas conveyed by a conveying apparatus of a biological safety cabinet, an amount of air conveyed, a filter operation duration and/or a ventilator operation duration in a biological safety cabinet, an intensity of a light source of a sample plate reader, a sensitivity of a photodetector, a time duration and/or a temperature of a sample plate reader, and a program parameter determining a movement and/or transport of laboratory samples on a worktop of a laboratory machine for treating fluid samples by transporting containers, by pipetting, a program parameter determining a division and/or dilution of laboratory samples in a laboratory machine for treating fluid samples, a program parameter determining a handling of a liquid sample in a laboratory machine for treating fluid samples.

2. The laboratory instrument according to claim 1, comprising a user interface apparatus for entering data by the user and with at least one indication apparatus for indicating information for the user on at least one graphical user interface, wherein the control apparatus is embodied to control the indication apparatus in such a way that a user-dependent design of the user interface is used, depending on the identified user and using the user-dependent configuration data.

3. The laboratory instrument according to claim 2, wherein the control apparatus controls the treatment as a function of at least one user parameter selected by a user and is embodied to acquire at least one user parameter in a user-dependent request process by means of the user interface apparatus, by virtue of
   i) presenting to the user at least one user-dependent on the user interface and
   ii) at least one user parameter being acquired by acquiring at least one entry of the user in the at least one request mask.

4. The laboratory instrument according to claim 1, wherein the control apparatus is embodied to transmit identification data, which identify the user, to the at least one external data processing apparatus via the at least one third data connection and to receive the configuration data assigned to the identified user as the user-dependent configuration data for the laboratory instrument from the external data processing apparatus.

5. The laboratory instrument according to claim 1, comprising
   a user interface apparatus in order to enable the identified user access to the laboratory instrument and
   wherein the access control device is configured to enable the identified user access by means of the user interface apparatus to the laboratory instrument via the first data connection.

6. The laboratory instrument according to claim 1, wherein the access control device is configured to enable the identified user access to the laboratory instrument only if at least one predetermined access condition in relation to the identified user is satisfied.

7. A system (300) for the instrument-controlled treatment of at least one laboratory sample, comprising: at least one laboratory instrument according to claim 1 and at least one external data processing apparatus, which are interconnected for interchanging configuration data.

8. The system according to claim 7, comprising at least a first and a second laboratory instrument according to claim 1, which are respectively configured to process first user-dependent configuration data, which can be used for the user-dependent control of the first laboratory instrument, and which can also be used for the user-dependent control of the second laboratory instrument.

9. The system according to claim 7, comprising an external data processing apparatus and comprising a user interface apparatus, by means of which user-dependent configuration data can be generated from the entries of the user.

10. A method (200) for configuring a laboratory instrument according to claim 1, wherein the configuration control device of the laboratory instrument comprises a control apparatus with an access control device, by means of which an identification of users can be performed, wherein data can be processed in the control apparatus, which data contain user-dependent configuration data for configuring the laboratory instrument, in particular for configuring a control program or process program used on the laboratory instrument, wherein the method comprises the following steps:
   identifying a user by means of the access control device of the control apparatus; and
   configuring the laboratory instrument or configuring a treatment using user-dependent configuration data.

* * * * *